/ ™

United States Patent
Halland et al.

(10) Patent No.: US 8,026,375 B2
(45) Date of Patent: Sep. 27, 2011

(54) TRANSITION METAL CATALYZED SYNTHESIS OF N-AMINOINDOLES

(75) Inventors: Nis Halland, Bad Soden (DE); Marc Nazare, Wiesbaden (DE); Andreas Lindenschmidt, Sulzbach (DE); Omar Rkyek, Tangier (MA); Matthias Urmann, Eschborn (DE); Jorge Alonso, Mannheim (DE)

(73) Assignee: Sanofi-Aventis, Paris (FR)

( * ) Notice: Subject to any disclaimer, the term of this patent is extended or adjusted under 35 U.S.C. 154(b) by 0 days.

(21) Appl. No.: 12/576,339

(22) Filed: Oct. 9, 2009

(65) Prior Publication Data

US 2010/0168429 A1 Jul. 1, 2010

Related U.S. Application Data

(63) Continuation of application No. PCT/EP2008/002519, filed on Mar. 29, 2008.

(30) Foreign Application Priority Data

Apr. 13, 2007 (EP) .................................. 07007585

(51) Int. Cl.
*C07D 471/04* (2006.01)
*C07D 209/04* (2006.01)
(52) U.S. Cl. ........................................ 548/483; 546/113
(58) Field of Classification Search .................. 546/113; 548/483
See application file for complete search history.

(56) References Cited

U.S. PATENT DOCUMENTS 6,346,621 B1   2/2002  Watanabe et al.
2006/0052624 A1*  3/2006  Galland et al. ................ 558/338

OTHER PUBLICATIONS

Prikhodko T.A. et al., "Heterocyclization of O-(Arylethynyl)Arylhydrazines as a New Procedure for the Synthesis of Substituted 1H- and 2H-Indazoles and Indoles", *Russian Chemical Bulletin, International Edition* 50(7):1268-1273 (2001).
Tang Z-Y et al., "Efficient Synthesis of 2-Substituted Indoles Based on Palladium(II) Acetate/Tri-Tert-Butylphospine-Catalyzed Alkynylation/Amination of 1,2-Dihalobenzenes", *Adv. Synth. Catal.* 348:846-850 (2006).
International Search Report dated Jul. 15, 2008 received from the European Patent Office issued in corresponding International Application No. PCT/EP2008/002519.

* cited by examiner

*Primary Examiner* — Joseph Kosack
(74) *Attorney, Agent, or Firm* — James W. Bolcsak; Scully, Scott, Murphy & Presser, P.C.

(57) ABSTRACT

The present invention relates to a process for the regioselective synthesis of compounds of the formula I,

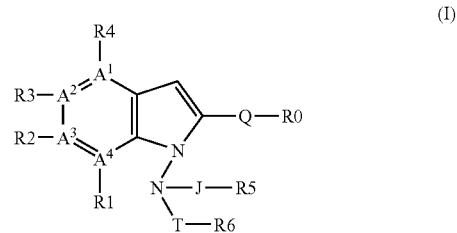

wherein R0; R1; R2; R3; R4; R5; R6; A1; A2; A3; A4, Q, T and J have the meanings indicated in the claims. The present invention provides a direct transition metal catalyzed process to a wide variety of multifunctional N-aminoindole or N-amino-azaindoles of the formula I from 2-halo-phenylacetylenes or (2-sulfonato)phenyl-acetylenes and N,N-disubstituted hydrazines, useful for the production of pharmaceuticals, diagnostic agents, liquid crystals, polymers, herbicides, fungicidals, nematicidals, parasiticides, insecticides, acaricides and arthropodicides.

11 Claims, No Drawings

TRANSITION METAL CATALYZED SYNTHESIS OF N-AMINOINDOLES

FIELD OF THE INVENTION

The present invention relates to a process for the regioselective synthesis of a compound of formula I,

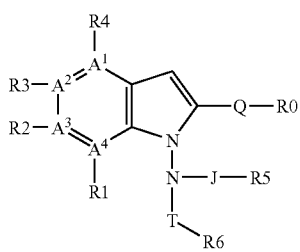

(I)

wherein R0, R1, R2, R3, R4, R5, R6, A1, A2, A3, A4, Q, T and J have the meanings indicated below and are useful as intermediates for the preparation of valuable pharmaceutically active ingredients.

BACKGROUND OF THE INVENTION

The present invention relates to a direct transition metal catalyzed process for the preparation of a variety of multifunctional substituted N-aminoindoles of formula I from 2-halo-phenylacetylenes or (2-sulfonato)phenylacetylenes and N,N-disubstituted hydrazines.

The Indole skeleton is found in numerous natural products as well as in the essential amino acid tryptophan and thus also in proteins. Indole derivatives display a vide variety of biological activities and can thus be regarded as a privileged structure in pharmaceutical research.

The ability of the indole scaffold to mediate an interaction with a variety of biological targets, is well-documented by a number of reports on the observed biological activity, as well as by the fact that many marketed drugs contain this heterocycle (J. A. Joule, in *Science of Synthesis* 2000, 10, 361ff and references therein). Examples of marketed drugs having an indole structural element include the anti-inflammatory indomethacin, the betablocker pindolol, the antimigraine agent sumitriptan and the 5-$HT_3$ antagonist ondansetron.

Of course the use of indoles or azaindoles is not limited to the above-mentioned pharmaceutical application and it is well known that indoles can be useful in numerous other applications. For example, 1H-indole-3-acetic acid is used as a plant growth regulator and 3-methyl-indole (skatol) and various other indoles are used as components in perfumes and fragrances. Also N-aminoindoles display various biological activities such as antidepressant (F. Schatz, U. Jahn, T. Wagner-Jauregg, L. Zimgibl, K. Thiele Arzneimittelforschung 1980, 30, 919-23), analgesic (U.S. Pat. No. 4,983,608), acetylcholinesterase inhibition (Klein et. al. *J. Med. Chem.* 1996, 39, 570-581), thrombin inhibition (J. J. Cui et al. *Bioorg. Med. Chem, Lett.* 2002, 12, 2925-2930) and $Ca^{2+}$-activated $K^+$ channel opening (S. Hu, C. A. Fink, H. S. Kim, R. W. Lappe *Drug. Dev. Res.* 1997, 41, 10) among others. Furthermore, several compounds are actively being developed as drugs e.g. Nerispirdine (WO 2005097199).

Due to the interesting physical and biological properties of indoles a large number of syntheses for their formation have been developed, but most protocols are multistep procedures performed under harsh conditions, but also milder transition metal catalyzed protocols have been described (G. R. Humprey, J. T. Kuethe *Chem. Rev.* 2006, 105, 2875-2911). Among the existing transition metal catalyzed indole syntheses only a few examples employs the coupling between amines and 2-halo-phenylacetylenes followed by subsequent cyclization (T. Konno, J. Chae, T. Ishihara, H. Yamanaka *J. Org. Chem.* 2004, 24, 8258-8265; J. Chae, T. Konno, T. Ishihara, H. Yamanaka *Chem. Lett.* 2004, 33, 314-315; L. Ackermann *Org. lett.* 2005, 7, 439-442; L. T. Kaspar, L. Ackermann *Tetrahedron* 2005, 61, 11311-11316) but no examples using hydrazines have been reported.

The absence of an efficient synthetic protocol for the formation of indoles and N-aminoindoles from easily available 2-halo-phenylacetylenes and hydrazines clearly demonstrates a lack of synthetic methodology, thereby hindering the synthesis and optimization of important compounds such as a potential drug substance or other compound with desired properties. Thus, the present invention can for example be useful in preparing intermediates or end products of biologically active compounds in pharmaceutical and agricultural applications.

SUMMARY OF THE INVENTION

The present invention provides a direct transition metal catalyzed synthetic route to a wide variety of multifunctional N-aminoindoles of formula I starting from 2-halo-phenylacetylenes or (2-sulfonate)phenylacetylenes of formula II and N,N-disubstituted hydrazines of formula III.

The advantages of the provided process are that it comprises a direct, catalytic, mild and versatile method for the synthesis of N-aminoindoles. Since the multi-step reaction proceeds as a one-pot domino reaction sequence using only a single catalyst, the process is very time- and cost-effective as well as being environmentally benign. Furthermore, the reaction conditions are compatible with a broad range of functional groups and a large variety of starting materials ensuring the generality of the reaction.

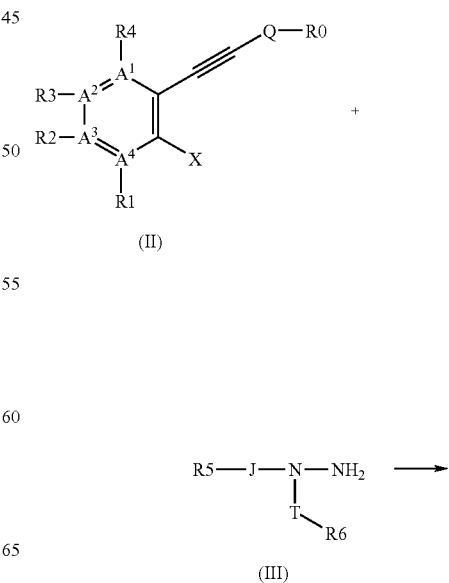

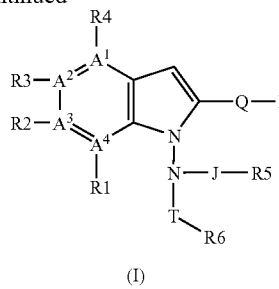

(I)

DETAILED DESCRIPTION OF THE INVENTION

A process for preparing a compound of formula I

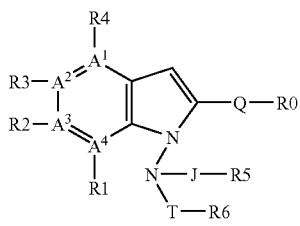

(I)

and/or all stereoisomeric forms of the compound of formula I, and/or mixtures of these forms in any ratio, and/or a physiologically tolerated salt of the compound of formula I, wherein A1, A2, A3 and A4 are independently from each other selected from a carbon or a nitrogen atom to form together with the two carbon atoms in formula I a stable aromatic or heteroaromatic ring;

Q is a covalent bond,
—$(C_1-C_6)$-alkylene, wherein alkylene is unsubstituted or mono-, di- or trisubstituted independently of one another by R14;
—$(C_3-C_8)$-cycloalkyl, wherein cycloalkyl is unsubstituted or mono-, di- or trisubstituted independently of one another by R14;
—$(C_6-C_{14})$-aryl, wherein aryl is unsubstituted or mono-, di-, tri- or four times substituted independently of one another by R13; or
—$(C_4-C_{14})$-heteroaryl, wherein heteroaryl is unsubstituted or mono-, di-, tri- or four times substituted independently of one another by R13;

J is a covalent bond,
—$(C_1-C_6)$-alkylene, wherein alkylene is unsubstituted or mono-, di- or trisubstituted independently of one another by R14;
—$(C_2-C_6)$-alkenylene, wherein alkenylene is unsubstituted or mono-, di- or trisubstituted independently of one another by R14,
—$(C_2-C_6)$-alkynylene, wherein alkynylene is unsubstituted or mono-, di- or trisubstituted independently of one another by R14,
—$(C_3-C_8)$-cycloalkyl, wherein cycloalkyl is unsubstituted or mono-, di- or trisubstituted independently of one another by R14;
—$(C_6-C_{14})$-aryl, wherein aryl is unsubstituted or mono-, di-, tri- or four times substituted independently of one another by R13; or
—$(C_4-C_{14})$-heteroaryl, wherein heteroaryl is unsubstituted or mono-, di-, tri- or four times substituted independently of one another by R13;

T is a covalent bond,
—$(C_1-C_6)$-alkylene, wherein alkylene is unsubstituted or mono-, di- or trisubstituted independently of one another by R14;
—$(C_3-C_8)$-cycloalkyl, wherein cycloalkyl is unsubstituted or mono-, di- or trisubstituted independently of one another by R14;
—$(C_6-C_{14})$-aryl, wherein aryl is unsubstituted or mono-, di-, tri- or four times substituted independently of one another by R13; or
—$(C_4-C_{14})$-heteroaryl, wherein heteroaryl is unsubstituted or mono-, di-, tri- or four times substituted independently of one another by R13;

R0, R1, R2, R3, R4, R5 and R6 are independent of one another identical or different and are
a) hydrogen atom,
b) —$(C_1-C_4)$-alkyl, wherein alkyl is unsubstituted or substituted one to three times by R13,
c) halogen,
d) phenyloxy-, wherein phenyloxy is unsubstituted or substituted one to three times by R13,
e) —$(C_1-C_3)$-fluoroalkyl,
f) —N(R10)-$(C_1-C_4)$-alkyl, wherein alkyl is unsubstituted or substituted one to three times by R13,
g) —$(C_6-C_{14})$-aryl, wherein aryl is unsubstituted or mono-, di-, tri- or four times substituted independently of one another by R13,
h) —$(C_4-C_{14})$-heteroaryl, wherein heteroaryl is unsubstituted or mono-, di-, tri- or four times substituted independently of one another by R13,
i) —$(C_3-C_8)$-cycloalkyl, wherein said cycloalkyl is unsubstituted or mono-, di-, tri- or four times substituted independently of one another by R13,
j) a 3- to 7-membered cyclic residue, containing 1, 2, 3 or 4 heteroatoms chosen from nitrogen, sulphur or oxygen, wherein said cyclic residue is unsubstituted or mono-, di-, tri- or four times substituted independently of one another by R13,
k) —O—$CF_3$,
l) —O—$(C_1-C_4)$-alkyl, wherein alkyl is unsubstituted or substituted one to three times by R13,
m) —$NO_2$,
n) —CN,
o) —OH,
p) —C(O)—R10,
q) —C(O)—O—R11,
r) —C(O)—N(R11)-R12,
s) —N(R11)-R12,
t) —N(R10)-$SO_2$—R10,
u) —S—R10,
v) —$SO_n$—R10, wherein n is 1 or 2,
w) —$SO_2$—N(R11)-R12, or
x) —O—$SO_2$—R13, or
y) at least one of R1, R2, R3 or R4 are absent in case one or more of A1, A2, A3 or A4 are nitrogen atom, or R1 and R2, R2 and R3 or R3 and R4 form together with the atoms which they are attached to a 5- or 8-membered ring, containing up to 0, 1, 2, 3 or 4 heteroatoms chosen from nitrogen, sulphur or oxygen, wherein said ring is unsubstituted or substituted one, two, three or four times by R14, R10 is hydrogen atom, —$(C_1-C_3)$-fluoroalkyl or —$(C_1-C_6)$-alkyl, R11 and R12 are independently of one another identical or different and are a) hydrogen atom,
b) —($C_1$-$C_6$)-alkyl, wherein alkyl is unsubstituted or mono-, di- or trisubstituted independently of one another by R13,
c) —($C_6$-$C_{14}$)-aryl-, wherein aryl is mono-, di- or trisubstituted independently of one another by R13, or
d) —($C_4$-$C_{14}$)-heteroaryl, wherein heteroaryl is unsubstituted or mono-, di- or trisubstituted independently of one another by R13, R13 is halogen, —$NO_2$, —CN, =O, —OH, —($C_1$-$C_8$)-alkyl, —($C_1$-$C_8$)-alkoxy, —$CF_3$, phenyloxy-, —C(O)—R10, —C(O)—O—R17, —C(O)—N(R17)-R18, —N(R17)-R18, —N(R10)-$SO_2$—R10, —S—R10, —$SO_n$—R10, wherein n is 1 or 2, —$SO_2$—N(R17)-R18, —($C_6$-$C_{14}$)-aryl, wherein aryl is unsubstituted or mono-, di- or trisubstituted independently of one another by R14, —($C_4$-$C_{14}$)-heteroaryl, wherein heteroaryl is unsubstituted or mono-, di- or trisubstituted independently of one another by R14, —($C_3$-$C_8$)-cycloalkyl, wherein said cycloalkyl is unsubstituted or mono-, di- or trisubstituted independently of one another by R14, or a 3- to 7-membered cyclic residue, containing up to 1, 2, 3 or 4 heteroatoms chosen from nitrogen, sulphur or oxygen, wherein said cyclic residue is unsubstituted or mono-, di- or trisubstituted independently of one another by R14, R14 is halogen, —OH, =O, —CN, —$CF_3$, —($C_1$-$C_8$)-alkoxy, —$NO_2$, —C(O)—OH, —N(R11)-R12, —C(O)—O—($C_1$-$C_4$)-alkyl, —($C_1$-$C_8$)-alkylsulfonyl, —C(O)—NH—($C_1$-$C_8$)-alkyl, —C(O)—N[($C_1$-$C_8$)-alkyl]$_2$, —C(O)—$NH_2$, —S—R10, —N(R10)-C(O)—NH—($C_1$-$C_8$)-alkyl, or —N(R10)-C(O)—N[$C_1$-$C_8$)-alkyl]$_2$, R17 and R18 are independently of one another identical or different and are
a) hydrogen atom,
b) —($C_1$-$C_6$)-alkyl,
c) —($C_6$-$C_{14}$)-aryl- or
d) —($C_4$-$C_{14}$)-heteroaryl, said process comprises reacting a compound of formula II

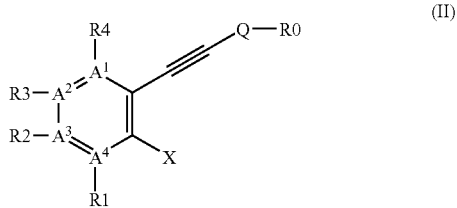

wherein R0, R1, R2, R3, R4, A1, A2, A3, R4 and Q are as defined in formula I and
X is Cl, Br, I, triflate, nonaflate, tosylate, alkyl sulfonate or aryl sulfonate,
with a compound of formula III or any salts thereof,

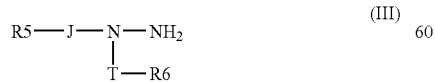

wherein J, T, R5 and R6 are as defined in formula I,
in the presence of a transition metal catalyst to give a compound of formula I and optionally the compound of formula I is converted to its physiologically tolerated salt.

2) The present invention also relates to a process for the preparation of selected compounds of formula I, wherein
A1, A2, A3 and A4 form together with the two carbon atoms in formula I a benzene, pyrazine, pyridazine, pyridine, pyrimidine, triazine or tetrazine,
Q is a covalent bond,
—($C_1$-$C_6$)-alkylene, wherein alkylene is unsubstituted or mono-, di- or trisubstituted independently of one another by R14;
—($C_3$-$C_6$)-cycloalkyl, wherein cycloalkyl is unsubstituted or mono-, di- or trisubstituted independently of one another by R14;
phenyl, wherein phenyl is unsubstituted or mono-, di-, tri- or four times substituted independently of one another by R13; or
—($C_4$-$C_{14}$)-heteroaryl, wherein heteroaryl is selected from acridinyl, azaindole (1H-pyrrolopyridinyl), azabenzimidazolyl, azaspirodecanyl, azepinyl, azetidinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, carbazolyl, 4aH-carbazolyl, carbolinyl, chromanyl, chromenyl, cinnolinyl, decahydrochinolinyl, 4,5-dihydrooxazolinyl, dioxazolyl, dioxazinyl, 1,3-dioxolanyl, 1,3-dioxolenyl, 3,3-dioxo[1,3,4]oxathiazinyl, 6H-1,5,2-dithiazinyl, dihydrofuro[2,3-b]-tetrahydrofuranyl, furanyl, furazanyl, imidazolidinyl, imidazolinyl, imidazolyl, indanyl, 1H-indazolyl, indolinyl, indolizinyl, indolyl, 3H-indolyl, isobenzofuranyl, isochromanyl, isoindazolyl, isoindolinyl, isoindolyl, isoquinolinyl, isothiazolyl, isothiazolidinyl, isothiazolinyl, isoxazolyl, isoxazolinyl, isoxazolidinyl, 2-isoxazolinyl, ketopiperazinyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, 1,2-oxathiepanyl, 1,2-oxathiolanyl, 1,4-oxazepanyl, 1,4-oxazepinyl, 1,2-oxazinyl, 1,3-oxazinyl, 1,4-oxazinyl, oxazolidinyl, oxazolinyl, oxazolyl, oxetanyl, oxocanyl, phenanthridinyl, phenanthrolinyl, phenazinyl, phenothiazinyl, phenoxathiinyl, phenoxazinyl, phthalazinyl, piperazinyl, piperidinyl, pteridinyl, purinyl, pyranyl, pyrazinyl, pyrazolidinyl, pyrazolinyl, pyrazolyl, pyrazolo[3,4-b]pyridine, pyridazinyl, pyridooxazolyl, pyridoimidazolyl, pyridothiazolyl, pyridinyl, pyridyl, pyrimidinyl, pyrrolidinyl, pyrrolidinonyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrahydrofuranyl, tetrahydropyranyl, tetrahydropyridinyl, tetrahydrothiophenyl, tetrazinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, 1,2-thiazinyl, 1,3-thiazinyl, 1,4-thiazinyl, 1,3-thiazolyl, thiazolyl, thiazolidinyl, thiazolinyl, thienyl, thietanyl, thienothiazolyl, thienooxazolyl, thienoimidazolyl, thietanyl, thiomorpholinyl, thiophenolyl, thiophenyl, thiopyranyl, 1,2,3-triazinyl, 1,2,4-triazinyl, 1,3,5-triazinyl, 1,2,3-triazolyl, 1,2,3-triazolyl, 1,2,4-triazolyl, 1,2,5-triazolyl, 1,3,4-triazolyl and xanthenyl, and wherein heteroaryl is unsubstituted or mono-, di-, tri- or four times substituted independently of one another by R13;
J is a covalent bond,
—($C_1$-$C_6$)-alkylene, wherein alkylene is unsubstituted or mono-, di- or trisubstituted independently of one another by R14;

—($C_2$-$C_6$)-alkenylene, wherein alkenylene is unsubstituted or mono-, di- or trisubstituted independently of one another by R14,
—($C_3$-$C_6$)-cycloalkyl, wherein cycloalkyl is unsubstituted or mono-, di- or trisubstituted independently of one another by R14;
phenyl, wherein phenyl is unsubstituted or mono-, di-, tri- or four times substituted independently of one another by R13; or
—($C_4$-$C_{14}$)-heteroaryl, wherein heteroaryl is as defined above and is unsubstituted or mono-, di-, tri- or four times substituted independently of one another by R13;
T is a covalent bond,
—($C_1$-$C_6$)-alkylene, wherein alkylene is unsubstituted or mono-, di- or trisubstituted independently of one another by R14;
—($C_3$-$C_6$)-cycloalkyl, wherein cycloalkyl is unsubstituted or mono-, di- or trisubstituted independently of one another by R14;
phenyl, wherein phenyl is unsubstituted or mono-, di-, tri- or four times substituted independently of one another by R13; or
—($C_4$-$C_{14}$)-heteroaryl, wherein heteroaryl is as defined above and is unsubstituted or mono-, di-, tri- or four times substituted independently of one another by R13;
R0, R1, R2, R3, R4, R5 and R6 are independent of one another identical or different and are
  a) hydrogen atom,
  b) F,
  c) Cl or Br,
  d) —($C_1$-$C_4$)-alkyl, wherein alkyl is unsubstituted or substituted one, two or three times by R13,
  e) —($C_1$-$C_3$)-fluoroalkyl,
  f) phenyl or naphthyl, wherein phenyl or naphthyl are unsubstituted or substituted one, two or three times by R13,
  g) —($C_4$-$C_{14}$)-heteroaryl, wherein heteroaryl is as defined above and is unsubstituted or mono-, di-, tri- or four times substituted independently of one another by R13, or
  h) —($C_3$-$C_6$)-cycloalkyl, wherein said cycloalkyl is unsubstituted or mono-, di-, tri- or four times substituted independently of one another by R13,
  i) a 3- to 7-membered cyclic residue selected from azepine, azetidine, aziridine, azirine, 1,4 diazepane, 1,2-diazepine, 1,3-diazepine, 1,4-diazepine, diaziridine, diazirine, dioxazole, dioxazine, dioxole, 1,3-dioxolene, 1,3-dioxolane, furan, imidazole, imidazoline, imidazolidine, isothiazole, isothiazolidine, isothiazoline, isoxazole, isoxazoline, isoxazolidine, 2-isoxazoline, ketomorpholine, ketopiperazine, morpholine, 1,2-oxa-thiepane, 1,2-oxathiolane, 1,4-oxazepane, 1,2-oxazine, 1,3-oxazine, 1,4-oxazine, oxazole, oxaziridine, oxetan, oxirane, piperazine, piperidine, pyran, pyrazine, pyrazole, pyrazoline, pyrazolidine, pyridazine, pyridine, pyrimidine, pyrrole, pyrrolidine, pyrrolidinone, pyrroline, tetrahydrofuran, tetrahydropyran, tetrahydropyridine, tetrazine, tetrazole, thiadiazine thiadiazole, 1,2-thiazine, 1,3-thiazine, 1,4-thiazine, 1,3-thiazole, thiazole, thiazolidine, thiazoline, thienyl, thietan, thiomorpholine, thiopyran, 1,2,3-triazine, 1,2,4-triazine, 1,3,5-triazine, 1,2,3-triazole or 1,2,4-triazole, and is unsubstituted or mono-, di-, tri- or four times substituted independently of one another by R13,
  j) —O—$CF_3$,
  k) —O—($C_1$-$C_4$)-alkyl, wherein alkyl is unsubstituted or substituted one, two or three times by R13,
  l) —N(R10)-($C_1$-$C_4$)-alkyl, wherein alkyl is unsubstituted or substituted one, two or three times by R13,
  m) —CN,
  n) —OH,
  o) phenyloxy-, wherein phenyloxy is unsubstituted or substituted one, two or three times by R13,
  p) —C(O)—O—R11,
  q) —C(O)—N(R11)-R12,
  r) —N(R11)-R12,
  s) —N(R10)-$SO_2$—R10,
  t) —S—R10,
  u) —$SO_n$—R10, wherein n is 1 or 2,
  v) —$SO_2$—N(R11)-R12,
  w) —C(O)—R10,
  x) —O—$SO_2$—R13, or
  y) at least one of R1, R2, R3 or R4 are absent in case one or more of A1, A2, A3 or A4 are nitrogen atom,
R10 is hydrogen atom, —($C_1$-$C_3$)-fluoroalkyl or —($C_1$-$C_6$)-alkyl,
R11 and R12 are independently of one another identical or different and are
  a) hydrogen atom,
  b) —($C_1$-$C_4$)-alkyl, wherein alkyl is unsubstituted or mono-, di- or trisubstituted independently of one another by R13,
  c) phenyl, wherein phenyl is unsubstituted or mono-, di- or trisubstituted independently of one another by R13,
  d) —($C_4$-$C_{14}$)-heteroaryl, wherein heteroaryl is as defined above and is unsubstituted or mono-, di- or trisubstituted independently of one another by R13,
R13 is F, Cl, —CN, =O, —OH, —($C_1$-$C_8$)-alkyl, —($C_1$-$C_8$)-alkoxy, —$CF_3$, phenyloxy-, —C(O)—R10, —C(O)—O—R17, —C(O)—N(R17)-R18, —N(R17)-R18, —N(R10)-$SO_2$—R10, —S—R10, —$SO_n$—R10, wherein n is 1 or 2, —$SO_2$—N(R17)-R18, phenyl, wherein phenyl is unsubstituted or mono-, di- or trisubstituted independently of one another by R14, —($C_4$-$C_{14}$)-heteroaryl, wherein heteroaryl is as defined above and is unsubstituted or mono-, di- or trisubstituted independently of one another by R14, —($C_3$-$C_6$)-cycloalkyl, wherein said cycloalkyl is unsubstituted or mono-, di- or trisubstituted independently of one another by R14, or a 3- to 7-membered cyclic residue, which is as defined above and is unsubstituted or mono-, di- or trisubstituted independently of one another by R14,
R14 is F, Cl, —OH, =O, —CN, —$CF_3$, —($C_1$-$C_8$)-alkyl, —($C_1$-$C_4$)-alkoxy, —C(O)—OH, —N(R11)-R12, —C(O)—O—($C_1$-$C_4$)-alkyl, —($C_1$-$C_8$)-alkylsulfonyl, —C(O)—$NH_2$, —C(O)—NH—($C_1$-$C_8$)-alkyl, —C(O)—N[($C_1$-$C_8$)-alkyl]$_2$, —S—R10, —N(R10)-C(O)—NH—($C_1$-$C_8$)-alkyl or —N(R10)-C(O)—N[($C_1$-$C_8$)-alkyl]$_2$,
R17 and R18 are independently of one another identical or different and are
  a) hydrogen atom,
  b) —($C_1$-$C_4$)-alkyl,
  c) phenyl or
  d) —($C_4$-$C_{14}$)-heteroaryl, wherein heteroaryl is as defined above, and X is Cl, Br, I, triflate, nonaflate or tosylate.
3) The present invention also relates to a process for the preparation of a compound of formula I, wherein
A1, A2, A3 and A4 form together with the two carbon atoms in formula I a benzene or pyridine,
Q is a covalent bond, methylene, ethylene, phenyl or pyridyl,
J is a covalent bond, methylene, ethylene, phenyl or pyridyl, T is a covalent bond, methylene, ethylene, phenyl or pyridyl,
R0, R1, R2, R3, R4, R5 and R6 are independent of one
another identical or different and are
a) hydrogen atom,
b) F,
c) Cl or Br,
d) —$(C_1$-$C_4)$-alkyl,
e) —$(C_1$-$C_3)$-fluoroalkyl,
f) phenyl,
g) pyridyl,
h) —$(C_3$-$C_6)$-cycloalkyl,
k) —O—$(C_1$-$C_4)$-alkyl, or
l) —C(O)—O—R11, or
m) at least one of R1, R2, R3 or R4 are absent in case one or more of A1, A2, A3 or A4 are nitrogen atom,
R11 is hydrogen atom or —$(C_1$-$C_4)$-alkyl, and
X is Cl, Br, I or tosylate.

The reaction can be performed in a broad range of protic or aprotic solvents, including polar aprotic solvents, or even in some cases without a solvent. Examples of said solvents are: tert-butanol, benzene, toluene, xylene, mesitylene, acetonitrile, propionitrile, tetrahydrofurane, 2-methyl-tetrahydrofurane, N,N-dimethylformamide, N-methylpyrrolidinone, N,N-dimethylacetamide, dimethylsulfoxide, 1,2-dimethoxyethane, tert-butylmethylether, triethylamine, diisopropylethylamine or pyridine. Preferred is N,N-dimethylacetamide, N,N-dimethylformamide, N-methylpyrrolidinone. Most preferred is N,N-dimethylformamide.

Useful bases for the process of the present invention is a basic organic or inorganic compound that acts as proton acceptor without inhibiting the catalytic activity of the employed transition metal catalyst. Suitable classes of such bases are for example carbonates, phosphates, alkoxides, hydroxides, amides, hydrides with a suitable metal as counter ion, or an alkali metal. Carbonates and phosphates are the preferred bases in the process of the present invention. Potassium carbonate or potassium phosphate and in particular caesium carbonate are the preferred bases. The bases can be used in pure form or a mixture of several bases can be used.

The bases are generally employed in moderate excess based on 2-halo-phenyl-acetylenes or (2-sulfonate)phenylacetylenes of formula II. A useful range is a 0.5 to 10 fold excess based on the 2-halo-phenylacetylenes or (2-sulfonate)phenyl-acetylenes of formula II. An even more useful range 1.1-2.0 fold excess based on the 2-halo-phenylacetylenes or (2-sulfonate)phenylacetylenes of formula II. The base may be favourably employed in a 1.4 fold excess based on the 2-halo-phenylacetylenes or (2-sulfonate)phenylacetylenes of formula II. In reactions where the hydrazine is employed as a salt, e.g. as a hydrochloride salt, one additional equivalent of base compared to the salt is added is added to the reaction mixture in order to generate the hydrazine in situ. Alternatively, the reaction can also be performed without a base if the hydrazine is used as the corresponding amide prepared by reaction of the hydrazine or hydrazine salt with a strong base.

The active form of the transition metal catalyst is not known. Therefore, the term "transition metal catalyst" in the present invention shall include any catalytic transition metal and/or catalyst precursor introduced into the reaction vessel and converted in situ into the active form, as well as the active form of the catalyst that promotes any part of the reaction. The transition metal catalyst can be used in any amount, but generally 0.00005-90 mol % would be employed. Preferred is the use of 0.01-20 mol %, and even more preferred is the use of 0.5-10 mol % and most preferably 1-5 mol % of the transition metal catalyst is employed.

Generally, any suitable transition metal catalyst that can mediate the reaction can be employed these include the elements of group 3-12 of the periodic table as well as the lanthanides. Preferred transition metals include platinum, palladium, nickel, gold, copper, iron, ruthenium, rhodium and iridium. Even more preferred are nickel and palladium and most preferred palladium. The transition metal catalyst can be soluble or insoluble, and the particular source of the transition metal useful in this process can be, but are not limited to: Pd-halides, Pd-halide complexes, Ni-halides, Ni-halide complexes, Pd-phosphine complexes, Ni-phosphine complexes, Pd-alkene complexes, Ni-alkene complexes, Pd-alkanoates, Pd-alkanoate complexes, Pd-acetonates, Ni-alkanoates, Ni-alkanoate complexes, Ni-acetonates, Raney nickel, Pd/C or Ni/C, or polymer supported palladium or nickel species or a mixture thereof. Representative examples include, but are not limited to: palladium (II) chloride, palladium (II) bromide, palladium (II) iodide, tris(dibenzylideneacetone)dipalladium (0), palladium (II) acetate, palladium (II) trifluoroacetate, tris(dibenzylideneacetone)dipalladium(0) chloroform adduct, bis(dibenzylideneacetone)palladium (0), bis(triphenylphosphine)palladium (II) chloride, tetrakis(triphenylphosphine)palladium (0), nickel (II) chloride, nickel (II) bromide, nickel (II) iodide, Ni(acac)$_2$, Ni(1,5-cyclooctadiene)$_2$, acetato(2'-di-tert-butylphosphino-1,1'-biphenyl-2-yl)palladium(II), (1,2-Bis(diphenylphosphino)ethane)di-chloropalladium(II), Bis[1,2-bis(diphenylphosphino)ethane] palladium (0), [(2S,3S)-Bis(diphenylphosphino)butane] [eta3-allyl]palladium(II) perchlorate, 1,3-bis(2,4,6-trimethylphenyl)imidazol-2-ylidene(1,4-naphthoquinone) palladium (0) dimmer, 2,2'-bis(diphenylphosphino)-1,1'-binaphthylpalladium(II) chloride.

The preferred transition metal sources are palladium (II) chloride, palladium (II) bromide, palladium (II) iodide, tris (dibenzylideneacetone)dipalladium(0), palladium (II) acetate, palladium (II) trifluoroacetate, tris(dibenzylideneacetone)dipalladium(0) chloroform adduct, bis(dibenzylideneacetone)palladium (0), bis(triphenylphosphine)-palladium (II) chloride, tetrakis(triphenylphosphine)palladium (0), and even more preferred are palladium (II) chloride, palladium (II) bromide, palladium (II) iodide, tris(dibenzylideneacetone)dipalladium(0). The most preferred palladium sources being palladium (II) chloride and tris(dibenzylideneacetone) dipalladium(0).

The group of ligands useful in this process may be chelating or non-chelating and may include alkyl or aryl phosphines or hybrids thereof e.g. dicyclohexlphenylphosphine, or aryl or alkyl diphosphines or hybrids thereof, diamines, imines, heterocyclic carbenes or hybrids thereof.

The ligand can be used in its free form or as a salt, e.g. the hydrochloride or tetrafluoroborate salt.

By way of example only, the ligand can be selected from the following compounds, but are not limited to: tri-tert-butylphosphine, tri-tert-butylphosphine tetrafluoroborate salt, tricyclohexylphosphine, dicyclohexlphenylphosphine, methyldiphenylphosphine, dimethylphenylphosphine, trimethylphosphine, triethylphosphine, triphenylphosphine, 2-dicyclohexylphosphino-2',4',6'-triisopropyl-1,1'-biphenyl, 2,2'-bis(di-tert-butylphosphino)-biphenyl, (+/−)-2,2'-bis (diphenylphosphino)-1,1'-binaphthalene, (9,9-dimethyl-9h-xanthene-4,5-diyl)bis[diphenyl phosphine], (R)-(−)-1-[(S)-2-(diphenylphosphino)ferrocenyl] ethyldicyclohexylphosphine, 1,2-bis(diphenylphosphino) ethane, 1,3-bis(diphenylphosphino)propane, (R)-(−)-1-[(S)-2-(dicyclohexylphosphino)ferrocenyl]-ethyldi-tert-butylphosphine, (R)-(+)-1,1'-bis(diphenylphosphino)-2,2'-bis(N,N-diiso-propylamido)ferrocene, (S,S)-1-[1-(di-tertbutylphosphino)ethyl]-2-(diphenyl-phosphino)-ferrocene, (1R,2R)-(+)-1,2-diaminocyclohexane-N,N'-bis(2-diphenyl-phosphino-1-naphtoyl, (−)-1,2-bis((2S,5S)-2,5-diisopropylphospholano)-benzene, bis[(2-diphenyl-phosphino)phenyl] ether, (S)-(−)-2,2'-Bis(di-para-tolylphosphino)-1,1'-binaphtyl, 4,5-bis(bis(3,5-bis(trifluoromethyl)phenyl)-phosphino)-9,9-dimethylxanthen.

Preferred ligands are tri-tert-butylphosphine, tri-tert-butylphosphine tetrafluoroborate salt, tricyclohexylphosphine, 2-dicyclohexylphosphino-2',4',6'-triisopropyl-1,1'-biphenyl. More preferred ligands are tri-tert-butylphosphine, tri-tert-butylphosphine tetrafluoro-borate salt, and most preferred is tri-tert-butylphosphine tetrafluoroborate salt.

Most favourably tri-tert-butylphosphine or tri-tert-butylphosphine tetrafluoroborate are employed in particular in combination with a palladium source bearing no phosphine itself, like e.g. palladium (II) chloride, palladium (II) bromide, palladium (II) iodide, or tris(dibenzylideneacetone)dipalladium(0).

The ligand can be used in any amount, but generally 0.00005-90 mol % would be employed. Preferred is the use of 0.01-40 mol %, and even more preferred is the use of 0.5-20 mol % and most preferably 1-10 mol % of the ligand is employed. The ratio of the ligand to the transition metal is generally about 1 to 20, preferably about 1-5 and most preferably 2.

The reaction step is usually carried out in the temperature range 0° C. to 300° C., preferably between 25° C. to 150° C., and most preferably between 80° C. to 130° C. Usually the reaction is carried out under the exclusion of air and moisture such as under an inert atmosphere like e.g. in an argon or nitrogen atmosphere at atmospheric pressure. The reaction time is normally in the range of 2 to 48 hours (h).

The progress of the reaction may be monitored by methods known to those skilled in the art, like for example thin layer silica gel chromatography, gas chromatography, nuclear magnetic resonance, infrared spectroscopy, and high pressure liquid chromatography combined with ultraviolet detection or mass spectroscopy. Preferably thin layer silica gel chromatography and high pressure liquid chromatography (HPLC) combined with mass spectroscopy are used.

The isolation and purification procedures useful for the compounds obtained by the process of the present invention are well-known to those skilled in the art, like for example filtration through a celite containing cartridge, aqueous work-up, extraction with organic solvents, distillation, crystallisation, chromatography on silica, and high pressure liquid chromatography on normal phase or reversed phase. Preferred methods include, but are not limited to those exemplified.

Examples of "—($C_1$-$C_8$)-alkyl" or "—($C_1$-$C_8$)-alkylene" are alkyl residues containing 1, 2, 3, 4, 5, 6, 7 or 8 carbon atoms, which are e.g. methyl, methylene, ethyl, ethylene, propylene, propyl, butyl, butylene, pentyl, pentylene, hexyl, heptyl or octyl, the n-isomers of all these residues, isopropyl, isobutyl, 1-methylbutyl, isopentyl, neopentyl, 2,2-dimethylbutyl, 2-methylpentyl, 3-methylpentyl, isohexyl, sec-butyl, tBu, tert-pentyl, sec-butyl, tert-butyl or tert-pentyl.

Examples of "—($C_2$-$C_6$)-alkenyl" or "—($C_2$-$C_6$)-alkenylene" are alkenyls containing 2, 3, 4, 5 or 6 carbon atoms, which are e.g. vinyl, 1-propenyl, 2-propenyl (=allyl), 2-butenyl, 3-butenyl, 2-methyl-2-butenyl, 3-methyl-2-butenyl, 5-hexenyl or 1,3-pentadienyl.

Examples of "—($C_2$-$C_6$)-alkynyl" or "—($C_2$-$C_6$)-alkynylene" are alkynyls containing 2, 3, 4, 5 or 6 carbon atoms, which are e.g. ethynyl, 1-propynyl, 2-propynyl or 2-butynyl.

The term "—($C_3$-$C_8$)-cycloalkyl" is understood as cyclic alkyl residues, which are cycloalkyl residues containing 3, 4, 5, 6, 7 or 8 ring carbon atoms like cyclopropyl, cyclobutyl, cyclopentyl, cyclohexyl, cycloheptyl or cyclooctyl, which can also be substituted and/or unsaturated. Unsaturated cyclic alkyl groups are e.g. cyclopentenyl or cyclohexenyl.

The term "alkyl sulfonate" is understood as an alkyl residue containing 1, 2, 3, 4, 5 or 6 carbon atoms substituted by sulfonate. Examples of such residues are methylsulfonate (mesylate), ethylsulfonate, propylsulfonate, butylsulfonate, pentylsulfonate or hexylsulfonate.

The term "A1, A2, A3, A4 are independently from each other selected from carbon or nitrogen atoms to form together with the two carbon atoms in formula I a stable aromatic or heteroaromatic ring" refers to a residue which can be derived from compounds such as benzene, pyrazine, pyridazine, pyridine, pyrimidine, triazine or tetrazine.

The term "—($C_6$-$C_{14}$)-aryl" is understood as meaning aromatic hydrocarbon radicals containing from 6 to 14 carbon atoms in the ring. Examples of —($C_6$-$C_{14}$)-aryl radicals are phenyl, naphthyl, for example 1-naphthyl and 2-naphthyl, biphenylyl, for example 2-biphenylyl, 3-biphenylyl and 4-biphenylyl, anthryl or fluorenyl. Biphenylyl radicals, naphthyl radicals and, in particular, phenyl radicals are preferred aryl radicals.

The term "aryl sulfonate" is understood as an aryl as defined herein, which is substituted by a sulfonate. Examples of such residues are benzenesulfonate, tosylate, nitrobenzenesulfonate or bromobenzenesulfonate.

The term "—($C_4$-$C_{14}$)-heteroaryl" refers to mono-, di- or tri-ring systems, wherein one or more of the 4 to 14 ring carbon atoms are replaced by one or more heteroatoms such as nitrogen, oxygen or sulphur. Examples are acridinyl, azaindole (1H-pyrrolopyridinyl), azabenzimidazolyl, azaspirodecanyl, azepinyl, azetidinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, carbazolyl, 4aH-carbazolyl, carbolinyl, chromanyl, chromenyl, cinnolinyl, decahydrochinolinyl, 4,5-dihydrooxazolinyl, dioxazolyl, dioxazinyl, 1,3-dioxolanyl, 1,3-dioxolenyl, 3,3-dioxo[1,3,4]oxathiazinyl, 6H-1,5,2-dithiazinyl, dihydrofuro[2,3-b]-tetrahydrofuranyl, furanyl, furazanyl, imidazolidinyl, imidazolinyl, imidazolyl, indanyl, 1H-indazolyl, indolinyl, indolizinyl, indolyl, 3H-indolyl, isobenzofuranyl, isochromanyl, isoindazolyl, isoindolinyl, isoindolyl, isoquinolinyl, isothiazolyl, isothiazolidinyl, isothiazolinyl, isoxazolyl, isoxazolinyl, isoxazolidinyl, 2-isoxazolinyl, ketopiperazinyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, 1,2-oxa-thiepanyl, 1,2-oxathiolanyl, 1,4-oxazepanyl, 1,4-oxazepinyl, 1,2-oxazinyl, 1,3-oxazinyl, 1,4-oxazinyl, oxazolidinyl, oxazolinyl, oxazolyl, oxetanyl, oxocanyl, phenanthridinyl, phenanthrolinyl, phenazinyl, phenothiazinyl, phenoxathiinyl, phenoxazinyl, phthalazinyl, piperazinyl, piperidinyl, pteridinyl, purinyl, pyranyl, pyrazinyl, pyrazolidinyl, pyrazolinyl, pyrazolyl, pyrazolo[3,4-b]pyridine, pyridazinyl, pyridooxazolyl, pyridoimidazolyl, pyridothiazolyl, pyridinyl, pyridyl, pyrimidinyl, pyrrolidinyl, pyrrolidinonyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrahydrofuranyl, tetrahydropyranyl, tetrahydropyridinyl, tetrahydrothio-phenyl, tetrazinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, 1,2-thiazinyl, 1,3-thiazinyl, 1,4-thiazinyl, 1,3-thiazolyl, thiazolyl, thiazolidinyl, thiazolinyl, thienyl, thietanyl, thienothiazolyl, thienooxazolyl, thienoimidazolyl, thietanyl, thiomorpholinyl, thiophenolyl, thiophenyl, thiopyranyl, 1,2,3-triazinyl, 1,2,4-triazinyl, 1,3,5-triazinyl, 1,2,3-triazolyl, 1,2,3-triazolyl, 1,2,4-triazolyl, 1,2,5-triazolyl, 1,3,4-triazolyl and xanthenyl.

The term "a 3- to 7-membered cyclic residue, containing 1, 2, 3 or 4 heteroatoms" refers to structures of heterocycles, which are e.g. azepine, azetidine, aziridine, azirine, 1,4 diazepane, 1,2-diazepine, 1,3-diazepine, 1,4-diazepine, diaziridine, diazirine, dioxazole, dioxazine, dioxole, 1,3-dioxolene, 1,3-dioxolane, furan, imidazole, imidazoline, imidazolidine, isothiazole, isothiazolidine, isothiazoline, isoxazole, isoxazoline, isoxazolidine, 2-isoxazoline, ketomorpholine, ketopiperazine, morpholine, 1,2-oxa-thiepane, 1,2-oxathiolane, 1,4-oxazepane, 1,2-oxazine, 1,3-oxazine, 1,4-oxazine, oxazole, oxaziridine, oxetan, oxirane, piperazine, piperidine, pyran, pyrazine, pyrazole, pyrazoline, pyrazolidine, pyridazine, pyridine, pyrimidine, pyrrole, pyrrolidine, pyrrolidinone, pyrroline, tetrahydrofuran, tetrahydropyran, tetrahydropyridine, tetrazine, tetrazole, thiadiazine thiadiazole, 1,2-thiazine, 1,3-thiazine, 1,4-thiazine, 1,3-thiazole, thiazole, thiazolidine, thiazoline, thienyl, thietan, thiomorpholine, thiopyran, 1,2,3-triazine, 1,2,4-triazine, 1,3,5-triazine, 1,2,3-triazole or 1,2,4-triazole.

The term "R1 and R2, R2 and R3 or R3 and R4 form together with the atoms which they are attached to a 5- or 8-membered ring, containing up to 0, 1, 2, 3 or 4 heteroatoms chosen from nitrogen, sulphur or oxygen" refers to residues which are e.g. azepine, azirine, azocane, azocane-2-one, cycloheptyl, cyclohexyl, cyclooctane, cyclooctene, 1,4-diazepane, 1,2-diazepine, 1,3-diazepine, 1,4-diazepine, [1,2]diazocan-3-one, [1,3]diazocan-2-one, [1,4]diazocane, dioxazine, dioxazole, [1,4]dioxocane, 1,3-dioxolane, dioxole, 1,3-dioxolene, furan, imidazole, imidazolidine, imidazoline, isothiazole, isothiazolidine, isothiazoline, isothiazole, isoxazole, isoxazolidine, isoxazoline, 2-isoxazoline, ketomorpholine, ketopiperazine, morpholine, 1,2-oxa-thiepane, 1,2-oxathiolane, 1,4-oxazepane, 1,2-oxazine, 1,3-oxazine, 1,4-oxazine, oxaziridine, [1,4]oxazocane, [1,3]oxazocan-2-one, oxocane, oxocan-2-one, oxazole, piperidine, piperazine, phenyl, pyridazine, pyridine, pyrimidine, pyran, pyrazine, pyrazole, pyrazolepyrrole, pyrazolidine, pyrazoline, pyridazine, pyridine, pyrimidine, pyrrole, pyrrolidine, pyrrolidinone, pyrroline, 5,6,7,8-tetrahydro-1H-azocin-2-one, tetrahydrofuran, tetrahydropyran, tetrahydropyridine, tetrazine, tetrazole, thiadiazine, thiadiazole, 1,2-thiazine, 1,3-thiazine, 1,4-thiazine, thiazole, 1,3-thiazole, thiazolidine, thiazoline, thienyl, thietan, thiomorpholine, thiopyran, 1,2,3-triazine, 1,2,4-triazine, 1,3,5-triazine, 1,2,3-triazole or 1,2,4-triazole.

The term "—($C_1$-$C_3$)-fluoroalkyl" is a partial or totally fluorinated alkyl-residue, which are e.g. —$CF_3$, —$CHF_2$, —$CH_2F$, —CHF—$CF_3$, —CHF—$CHF_2$, —CHF—$CH_2F$, —$CH_2$—$CF_3$, —$CH_2$—$CHF_2$, —$CH_2$—$CH_2F$, —$CF_2$—$CF_3$, —$CF_2$—$CHF_2$, —$CF_2$—$CH_2F$, —$CH_2$—CHF—$CF_3$, —$CH_2$—CHF—$CHF_2$, —$CH_2$—CHF—$CH_2F$, —$CH_2$—$CH_2$—$CF_3$, —$CH_2$—$CH_2$—$CHF_2$, —$CH_2$—$CH_2$—$CH_2F$, —$CH_2$—$CF_2$—$CF_3$, —$CH_2$—$CF_2$—$CHF_2$, —$CH_2$—$CF_2$—$CH_2F$, —CHF—CHF—$CF_3$, —CHF—CHF—$CHF_2$, —CHF—CHF—$CH_2F$, —CHF—$CH_2$—$CF_3$, —CHF—$CH_2$—$CHF_2$, —CHF—$CH_2$—$CH_2F$, —CHF—$CF_2$—$CF_3$, —CHF—$CF_2$—$CHF_2$, —CHF—$CF_2$—$CH_2F$, —$CF_2$—CHF—$CF_3$, —$CF_2$—CHF—$CHF_2$, —$CF_2$—CHF—$CH_2F$, —$CF_2$—$CH_2$—$CF_3$, —$CF_2$—$CH_2$—$CHF_2$, —$CF_2$—$CH_2$—$CH_2F$, —$CF_2$—$CF_2$—$CF_3$, —$CF_2$—$CF_2$—$CHF_2$ or —$CF_2$—$CF_2$—$CH_2F$.

Halogen is fluorine, chlorine, bromine or iodine, preferably fluorine, chlorine or bromine, particularly preferably chlorine or bromine.

The term "triflate" refers to trifluoro-methanesulfonic acid ester or trifluoromethanesulfonate.

The term "nonaflate" refers to 1,1,2,2,3,3,4,4,4-nonafluoro-1-butanesulfonic acid ester or 1,1,2,2,3,3,4,4,4-nonafluoro-1-butanesulfonate.

The term "at least one of R1, R2, R3 or R4 are absent in case one or more of A1, A2, A3 or A4 are nitrogen atom," refers to a residue wherein the nitrogen atom is not substituted by any residue, e.g. in case A1 is nitrogen atom and A2, A3 and A4 are each a carbon atom and R4 is absent and R1, R2 and R3 are each a hydrogen atom the residue pyridine is formed. If R1, R2 and R3 are not each a hydrogen atom but one of the residues specified under b) to x) then a substituted pyridine residue is formed. In case A1 and A2 are each a nitrogen atom and A3 and A4 are each a carbon atom and R4 and R3 are absent and R1 and R2 are each a hydrogen atom the residue pyridazine is formed. If R1 and R2 are not each a hydrogen atom but one of the residues specified under b) to x) then a substituted pyridazine residue is formed.

Optically active carbon atoms present in the compounds of the formula (I) can independently of each other have R configuration or S configuration. The compounds of the formula (I) can be present in the form of pure enantiomers or pure diastereomers or in the form of mixtures of enantiomers and/or diastereomers, for example in the form of racemates. The present invention relates to pure enantiomers and mixtures of enantiomers as well as to pure diastereomers and mixtures of diastereomers. The invention comprises mixtures of two or of more than two stereoisomers of the formula (I), and it comprises all ratios of the stereoisomers in the mixtures. In case the compounds of the formula (I) can be present as E isomers or Z isomers (or cis isomers or trans isomers) the invention relates both to pure E isomers and pure Z isomers and to E/Z mixtures in all ratios. The invention also comprises all tautomeric forms of the compounds of the formula (I).

Diastereomers, including E/Z isomers, can be separated into the individual isomers, for example, by chromatography. Racemates can be separated into the two enantiomers by customary methods, for example by chromatography on chiral phases or by resolution, for example by crystallization of diastereomeric salts obtained with optically active acids or bases. Stereochemically uniform compounds of the formula (I) can also be obtained by employing stereochemically uniform starting materials or by using stereoselective reactions.

The starting materials or building blocks for use in the general synthetic procedures that can be applied in the preparation of the compounds of formula (I) are readily available to one of ordinary skill in the art. In many cases they are commercially available or have been described in the literature. Otherwise they can be prepared from readily available precursor compounds analogously to procedures described in the literature, or by procedures or analogously to procedures described in this application.

Furthermore, in order to obtain the desired substituents in the benzene nucleus and in the heterocyclic nucleus of the N-aminoindole or N-aminoazaindole ring system in the formula (I), the functional groups introduced into the ring system during the N-aminoindole or N-aminoazaindole synthesis can be chemically modified.

Especially the groups present in the N-aminoindole or N-aminoazaindole ring system can be modified by a variety of reactions and thus the desired residues R0, R1, R2, R3, R4, R5 and R6 be obtained. For example, ester groups present in the benzene nucleus can be hydrolyzed to the corresponding carboxylic acids, which after activation can then be reacted with amines or alcohols under standard conditions. Ether groups present at the benzene nucleus, for example benzyloxy groups or other easily cleavable ether groups, can be cleaved to give hydroxyl groups which then can be reacted with a variety of agents, for example etherification agents or activating agents allowing replacement of the hydroxyl group by other groups. Sulphur-containing groups can be reacted analogously.

Due to the fact that in the present case the functional groups are attached to an N-aminoindole or N-aminoazaindole ring it may in certain cases become necessary to specifically adapt reaction conditions or to choose specific reagents from a variety of reagents that can in principle be employed into a conversion reaction, or otherwise to take specific measures for achieving a desired conversion, for example to use protection group techniques. However, finding out suitable reaction variants and reaction conditions in such cases does not cause any problems for one skilled in the art.

In the course of the preparation of the compounds of the formula I it can generally be advantageous or necessary to introduce functional groups which reduce or prevent undesired reactions or side reactions in the synthesis, in the form of precursor groups which are later converted into the desired functional groups, or to temporarily block functional groups by a protective group strategy suited to the synthesis problem. Such strategies are well known to those skilled in the art. As an example of a precursor group, cyano groups could be mentioned which in a later step can be transformed into carboxylic acid derivatives or by reduction into aminomethyl groups. Protective groups can also have the meaning of a solid phase, and cleavage from the solid phase stands for the removal of the protective group. The use of such techniques is known to those skilled in the art, e.g. a phenolic hydroxyl group can be attached to a trityl-polystyrene resin, which serves as a protecting group, and the molecule is cleaved from this resin by treatment with TFA at a later stage of the synthesis.

In the course of the synthesis the employment of microwave assistance for speeding-up, facilitating or enabling reactions may be beneficial or even required in many cases. Some reactions are for example described by P. Lidstrom, J. Tierney, B. Wathey, J. Westman, Tetrahedron, 57 (2001), 9225.

Physiologically tolerable salts of the compounds of formula I are non-toxic salts that are physiologically acceptable, in particular, pharmaceutically utilizable salts. Such salts of compounds of formula I containing acidic groups, for example, a carboxyl group (COOH), include, for example, alkali metal salts or alkaline earth metal salts, such as sodium salts, potassium salts, magnesium salts and calcium salts, as well as salts with physiologically tolerable quaternary ammonium ions, such as tetramethylammonium or tetraethylammonium, and acid addition salts with ammonia and physiologically tolerable organic amines, such as methylamine, dimethylamine, trimethylamine, ethylamine, triethylamine, ethanolamine or tris-(2-hydroxyethyl)amine. Basic groups contained in the compounds of formula I, for example, amino groups or guanidino groups, form acid addition salts, for example, with inorganic acids such as hydrochloric acid, hydrobromic acid, sulfuric acid, nitric acid or phosphoric acid, or with organic carboxylic acids and sulfonic acids such as formic acid, acetic acid, oxalic acid, citric acid, lactic acid, malic acid, succinic acid, malonic acid, benzoic acid, maleic acid, fumaric acid, tartaric acid, methanesulfonic acid or p-toluenesulfonic acid. Compounds of the formula I which simultaneously contain a basic group and an acidic group, for example, a guanidino group and a carboxyl group, can also be present as zwitterions (betaines) which are likewise included in the scope of the present invention. Salts of compounds of formula I can be obtained by customary methods known to those skilled in the art, for example, by combining a compound of the formula I with an inorganic or organic acid or base in a solvent or dispersant, or from other salts by cation exchange or anion exchange. The present invention also includes all salts of the compounds of formula I which, because of low physiologically tolerability, are not directly suitable for use in pharmaceuticals but are suitable, for example, as intermediates for carrying out further chemical modifications of the compounds of formula I or as starting materials for the preparation of physiologically tolerable salts.

A further aspect of the invention is the use of a compound of the formula I as prepared by the process according to the invention for the production of pharmaceuticals, diagnostic agents, liquid crystals, polymers, herbicides, fungicidals, nematicidals, parasiticides, insecticides, acaricides and arthropodicides.

Furthermore, the compounds of the formula I can be used as synthesis intermediates for the preparation of other compounds, in particular of other pharmaceutical active ingredients, which are obtainable from the compounds of the formula I, for example by introduction of substituents or modification of functional groups.

The general synthetic sequences for preparing the compounds useful in the present invention are outlined in the examples given below. Both an explanation of, and the actual procedure for, the various aspects of the present invention are described where appropriate. Those with skill in the art will readily understand that known variations of the conditions and processes described in the examples can be used to synthesize the compounds of the present invention.

EXAMPLES

When in the final step of the synthesis of a compound an acid such as trifluoroacetic acid or acetic acid was used, for example when trifluoroacetic acid was employed to remove a tBu group or when a compound was purified by chromatography using an eluent which contained such an acid, in some cases, depending on the work-up procedure, for example the details of a freeze-drying process, the compound was obtained partially or completely in the form of a salt of the acid used, for example in the form of the acetic acid salt or trifluoroacetic acid salt or hydrochloric acid salt.

Abbreviations used:

| | |
|---|---|
| tert-Butyl | tBu |
| N,N-dimethylformamide | DMF |
| Ethylacetate | EtOAc |
| Fast Atom Bombardement | FAB |
| Liquid chromatography with mass spectrometry | LC-MS |
| Room temperature 21° C. to 24° C. | RT |
| Trifluoroacetate | TFA |

General procedure for the one-pot formation of N-aminoindoles from 2-haloacetylenes and N,N-disubstituted hydrazines: To an oven dried reaction tube containing a magnetic stirring bar was added the Pd source, ligand, solvent and base. The reaction tube was sealed with a septum and stirred for 30 min at RT under an inert atmosphere (nitrogen or argon) prior to addition of the reagents. The reagents were added and the mixture heated to desired temperature and reaction progress was followed by LC-MS. Upon completion of the reaction as judged by LCMS, the reaction mixture was allowed to cool to RT and quenched with $NaHCO_3$ (saturated aqueous) and extracted with EtOAc. The organic phase was dried over $Na_2SO_4$ followed by filtration, or by filtering through a Varian cartridge Chem Elut 12198007, before the solvent was removed by rotary evaporation and the residue purified by flash chromatography on silica using CH$_2$Cl$_2$/heptane/EtOAc mixtures. After removal of the organic solvents by rotary evaporation the desired N-aminoindole was obtained in high purity.

Example 1

Phenyl-(2-phenyl-indol-1-yl)-carbamic acid tert-butyl ester

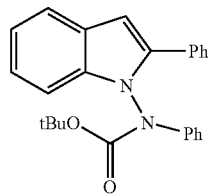

Following the general procedure outlined above, a reaction tube was charged with 4.4 mg PdCl$_2$ (5 mol %), 14.5 mg tBu$_3$PHBF$_4$ (10 mol %), 228.1 mg Cs$_2$CO$_3$ (1.4 equiv.) and 2.5 mL DMF. After stirring for 30 min at RT under a flow of argon, 1-chloro-2-phenylethynyl-benzene (106.3 mg, 1.0 equiv.) and N-phenylhydrazine carboxylic acid tert-butyl ester (145.8 mg, 1.4 equiv.) were added and the reaction was heated to 110° C. for 3 hours. After cooling to RT, the reaction mixture was quenched with 30 mL NaHCO$_3$ (saturated aqueous) and extracted with EtOAc (2×30 mL) and the organic phase was dried by eluting through a Varian Chem Elut 12198007 cartridge. Removal of the solvents afforded the crude N-aminoindole as a dark-brown oil that was purified by flash chromatography on silica using CH$_2$Cl$_2$/heptane to afford 164.8 mg (86%) of Phenyl-(2-phenyl-indol-1-yl)-carbamic acid tert-butyl ester as a yellowish oil. $^1$H-NMR (DMSO-d$_6$) δ 1.25 (s, 9H), 6.85 (s, 1H), 7.10-7.14 (m, 3H), 7.15-7.18 (m, 1H), 7.23 (d, 2H, J=4.0 Hz), 7.26-7.30 (m, 2H), 7.39-7.41 (m, 1H), 7.44 (t, J=7.2 Hz, 2H), 7.52 (d, 2H, J=7.9 Hz), 7.65 (d, 1H, J=7.8 Hz); $^{13}$C-NMR (DMSO-d$_6$) δ 27.3, 82.5, 101.4, 109.2, 120.8, 121.0, 123.1, 125.3, 125.7, 127.4, 128.4, 128.7, 128.8, 130.5, 136.7, 139.7, 140.9, 152.0; HRMS (FAB): Calculated for C$_{25}$H$_{25}$N$_2$O$_2$ (M+H$^+$) 385.1916. found 385.1917.

Example 2

(6-Fluoro-2-phenyl-indol-1-yl)phenyl-carbamic acid tert-butyl ester

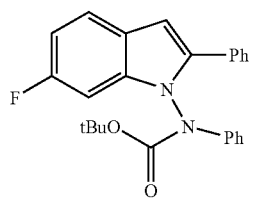

The reaction was performed according to example 1 using 115.3 mg 2-chloro-4-fluoro-1-phenylethynyl-benzene and a reaction temperature of 110° C. for 3 hours. This afforded 189.6 mg (94%) of the title compound. $^1$H-NMR (DMSO-d$_6$) δ 1.27 (s, 9H), 6.87 (s, 1H), 7.03 (ddd, 1H, J=9.8, 8.6, 2.3 Hz), 7.07-7.16 (m, 4H), 7.29 (t, 2H, J=7.9 Hz), 7.39-7.42 (m, 1H), 7.43-7.47 (m, 2H), 7.49-7.52 (m, 2H), 7.66 (dd, 1H, J=8.7, 5.3 Hz); $^{13}$C-NMR (DMSO-d$_6$) δ 27.3, 82.7, 95.9 (d, J=27.2 Hz), 101.4, 109.7 (d, J=24.3 Hz), 121.2, 122.2 (d, J=9.9 Hz), 122.3, 125.5, 127.4, 128.5, 128.8, 128.9, 136.9 (d, J=11.9 Hz), 140.5 (d, J=4.3 Hz), 140.6, 151.8, 159.7 (d, J=238.6 Hz); HRMS (FAB): Calculated for C$_{25}$H$_{24}$N$_2$O$_2$F (M+H$^+$) 403.1822. found 403.1815.

Example 3

Phenyl-(2-phenyl-5-trifluoromethyl-indol-1-yl)-carbamic acid tert-butyl ester

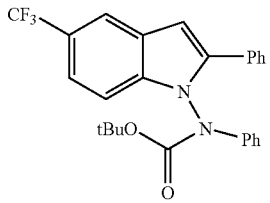

The reaction was performed according to example 1 using 140.3 mg 1-Chloro-2-phenylethynyl-4-trifluoromethyl-benzene and a reaction temperature of 110° C. for 3 hours. This afforded 203.5 mg (90%) of the title compound. $^1$H-NMR (DMSO-d$_6$) δ 1.25 (s, 9H), 7.03 (s, 1H), 7.11-7.17 (m, 3H), 7.30 (t, 2H, J=7.9 Hz), 7.41-7.49 (m, 4H), 7.52-7.56 (m, 3H), 8.08 (s, 1H); $^{13}$C-NMR (DMSO-d$_6$) δ 27.3, 83.0, 102.1, 110.1, 118.5, 119.7, 122.2 (q, J=31.3 Hz), 125.1 (q, J=271.6 Hz), 125.2, 125.6, 127.6, 128.3 (q, J=39.0 Hz), 128.9, 129.0, 129.8, 138.1, 140.6, 141.7, 151.7; HRMS (FAB): Calculated for C$_{26}$H$_{24}$N$_2$O$_2$F$_3$ (M+H$^+$) 453.1790. found 453.1785.

Example 4

(6-Methoxy-2-phenyl-indol-1-yl)phenyl-carbamic acid tert-butyl ester

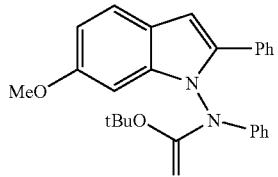

The reaction was performed according to example 1 using 121.4 mg 2-chloro-4-methoxy-1-phenylethynyl-benzene and a reaction temperature of 110° C. for 5 hours. This afforded 205.6 mg (99%) of the title compound. $^1$H-NMR (DMSO-d$_6$) δ 1.27 (s, 9H), 3.74 (s, 3H), 6.67 (d, 1H, J=1.9 Hz), 6.76 (d, 1H, J=0.6 Hz), 6.83 (dd, 1H, J=8.5, 2.2 Hz), 7.10-7.13 (m, 3H), 7.27 (t, 2H, J=7.8 Hz), 7.33-7.37 (m, 1H), 7.41 (t, 2H, J=7.6 Hz), 7.45-7.48 (m, 2H), 7.53 (d, 1H, J=8.5 Hz); $^{13}$C-NMR (DMSO-d$_6$) δ 27.3, 55.3, 82.4, 92.8, 101.3, 110.5, 119.7, 121.0, 121.6, 125.2, 127.1, 127.9, 128.6, 128.8, 130.8, 137.8, 138.5, 140.8, 151.9, 156.8; HRMS (FAB): Calculated for C$_{26}$H$_{27}$N$_2$O$_3$ (M+H$^+$) 415.2022. found 415.2028.

Example 5

Methyl-(2-phenyl-indol-1-yl)-carbamic acid tert-butyl ester

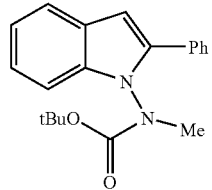

The reaction was performed according to example 1 using 73.1 mg N-methyl-hydrazine carboxylic acid tert-butyl ester and a reaction temperature of 110° C. for 3 hours. This afforded 107.2 mg (67%) of the title compound as a 2:1 mixture of rotamers. $^1$H-NMR (DMSO-d$_6$) δ 1.08 (s, 6H), 1.48 (s, 3H), 3.09 (s, 1H), 3.27 (s, 2H), 6.72 (s, 1H), 7.15 (t, 1H, J=7.9 Hz), 7.22-7.31 (m, 2H), 7.41-7.45 (m, 1H), 7.51 (t, 2H, J=7.0 Hz), 7.54-7.59 (m, 2H), 7.61 (d, 1H, J=7.6 Hz); $^{13}$C-NMR (DMSO-d$_6$) δ 27.3, 27.7, 36.9, 37.8, 80.6, 81.5, 100.6, 100.8, 108.9, 109.0, 120.6, 120.9, 122.7, 125.7, 127.5, 128.2, 128.7, 130.6, 130.8, 135.9, 136.3, 139.3, 139.7, 153.8, 154.1; HRMS (FAB): Calculated for C$_{20}$H$_{23}$N$_2$O$_2$ (M+H$^+$) 323.1760. found 323.1761.

Example 6

Phenyl-(2-phenyl-indol-1-yl)-carbamic acid ethyl ester

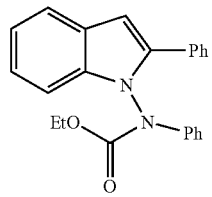

The reaction was performed according to example 1 using 126.1 mg N-phenyl-hydrazine carboxylic acid ethyl ester and a reaction temperature of 110° C. for 3 hours. This afforded 154.4 mg (87%) of the title compound. $^1$H-NMR (DMSO-d$_6$) δ 1.06 (br t, 3H, J=6.7 Hz), 4.21 (m, 2H), 6.86 (s, 1H), 7.06 (d, 2H, J=7.8 Hz), 7.12 (t, 1H, J=7.4 Hz), 7.17 (t, 1H, J=7.4 Hz), 7.22-7.28 (m, 3H), 7.33 (d, 1H, J=8.0 Hz), 7.38-7.42 (m, 1H), 7.45 (t, 1H, J=7.4 Hz), 7.50-7.53 (m, 2H), 7.65 (d, 1H, J=7.8 Hz); $^{13}$C-NMR (DMSO-d$_6$) δ 14.0, 62.8, 101.7, 109.4, 120.8, 121.3, 121.4, 123.2, 125.6, 125.8, 127.4, 128.4, 128.8, 128.9, 130.4, 136.5, 139.3, 140.6, 153.6; HRMS (FAB): Calculated for C$_{23}$H$_{21}$N$_2$O$_2$ (M+H$^+$) 357.1603. found 357.1595.

Example 7

Phenyl-(2-pyridin-2-yl-indol-1-yl)-carbamic acid tert-butyl ester

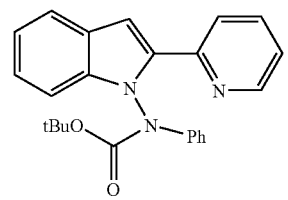

The reaction was performed according to example 1 using 106.8 mg 2-(2-chloro-phenylethynyl)-pyridine and a reaction temperature of 110° C. for 3 hours. This afforded 154.0 mg (80%) of the title compound. $^1$H-NMR (DMSO-d$_6$) δ 1.23 (br s, 9H), 7.05-7.09 (m, 1H), 7.15 (t, 1H, J=7.4 Hz), 7.22-7.31 (m, 8H), 7.67 (d, 1H, J=7.8 Hz), 7.86 (dt, 1H, J=1.7, 7.4 Hz), 7.92 (d, 1H, J=8.0 Hz), 8.53 (d, 1H, J=4.7 Hz); $^{13}$C-NMR (DMSO-d$_6$) δ 27.4, 81.5, 102.9, 109.1, 121.1, 121.6, 121.8, 122.5, 123.9, 124.7, 124.8, 128.4, 136.7, 136.8, 137.2, 141.4, 149.1, 149.8, 151.9; HRMS (FAB): Calculated for C$_{24}$H$_{24}$N$_3$O$_2$ (M+H$^+$) 386.1869. found 386.1874.

Example 8

1-(tert-Butoxycarbonyl-phenyl-amino)-1H-indole-2-carboxylic acid tert-butyl ester

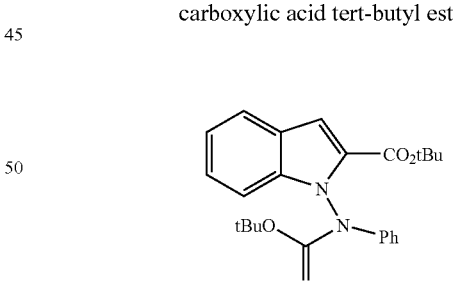

The reaction was performed according to example 1 using 118.4 mg (2-chloro-phenyl)-propynoic acid tert-butyl ester and a reaction temperature of 110° C. for 3 hours. This afforded 135.7 mg (64%) of the title compound. $^1$H-NMR (DMSO-d$_6$) δ 1.32 (br s, 9H), 1.46 (s, 9H), 7.15 (t, 1H, J=7.2 Hz), 7.20 (t, 1H, J=7.4 Hz), 7.26-7.30 (m, 3H), 7.33 (d, 1H, J=8.0 Hz), 7.36 (d, 1H, J=8.5 Hz), 7.75 (d, 1H, J=8.0 Hz); $^{13}$C-NMR (DMSO-d$_6$) δ 27.5, 27.7, 81.4, 82.0, 109.4, 109.9, 120.9, 121.7, 122.6, 123.2, 124.9, 126.3, 128.3, 128.5, 137.4, 141.0, 151.6, 158.8; HRMS (FAB): Calculated for $C_{24}H_{28}N_2O_4Na$ (M+Na$^+$) 431.1947. found 431.1952.

Example 9

Phenyl-(2-phenyl-pyrrolo[3,2-c]pyridin-1-yl)-carbamic acid tert-butyl ester

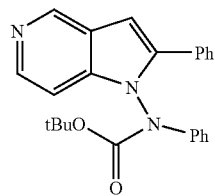

The reaction was performed according to example 1 using 106.8 mg 4-chloro-3-phenylethynyl-pyridine and a reaction temperature of 110° C. for 3 hours. This afforded 172.4 mg (89%) of the title compound. $^1$H-NMR (DMSO-d$_6$) δ 1.26 (br s, 9H), 7.00 (s, 1H), 7.10-7.17 (m, 3H), 7.26-7.36 (m, 3H), 7.42-7.51 (m, 3H), 7.51-7.55 (m, 2H), 8.32 (d, 1H, J=5.5 Hz), 8.94 (br s, 1H); $^{13}$C-NMR (DMSO-d$_6$) δ 27.3, 82.9, 100.3, 104.6, 121.2, 122.3, 125.7, 127.7, 128.8, 129.0, 129.7, 140.4, 140.5, 140.7, 142.2, 143.4, 151.5; HRMS (FAB): Calculated for $C_{24}H_{24}N_3O_2$ (M+H$^+$) 386.1869. found 386.1882.

Example 10

1-(tert-Butoxycarbonyl-phenyl-amino)-2-cyclopropyl-1H-indole-6-carboxylic acid tert-butyl ester

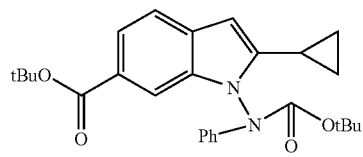

The reaction was performed according to example 1 using 138.4 mg 3-Chloro-4-cyclopropylethynyl-benzoic acid tert-butyl ester and a reaction temperature of 110° C. for 3 hours. This afforded 196.0 mg (87%) of the title compound. $^1$H-NMR (DMSO-d$_6$) δ 0.67-0.77 (m, 2H), 0.85-0.92 (m, 1H), 1.01-1.07 (m, 1H), 1.35 (s, 9H), 1.52 (s, 9H), 1.71-1.77 (m, 1H), 6.28 (s, 1H), 7.21 (t, 1H, J=7.4 Hz), 7.30 (d, 2H, J=7.5 Hz), 7.38 (d, 1H, J=7.4 Hz), 7.40 (d, 1H, J=7.3 Hz), 7.55 (d, 1H, J=8.2 Hz), 7.64 (dd, 1H, J=8.3, 1.5 Hz), 7.68 (s, 1H); $^{13}$C-NMR (DMSO-d$_6$) δ 6.5, 7.4, 7.9, 27.4, 27.8, 80.1, 82.7, 96.1, 109.0, 119.7, 121.3, 124.6, 125.5, 129.0, 129.1, 135.1, 140.9, 147.1, 151.7, 165.5; HRMS (FAB): Calculated for $C_{27}H_{33}N_2O_4$ (M+H$^+$) 449.2440. found 449.2459.

The invention claimed is:

1. A process for preparing a compound of formula I

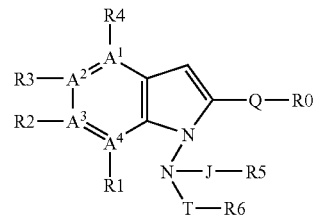

and/or all stereoisomeric forms of the compound of formula I, and/or mixtures of these forms in any ratio, and/or a physiologically tolerated salt of the compound of formula I, wherein A1, A2, A3 and A4 are independently from each other selected from a carbon or a nitrogen atom to form together with the two carbon atoms in formula I a stable aromatic or heteroaromatic ring;

Q is selected from a covalent bond;
—($C_1$-$C_6$)-alkylene, wherein alkylene is unsubstituted or mono-, di- or trisubstituted independently of one another by R14;
—($C_3$-$C_8$)-cycloalkyl, wherein cycloalkyl is unsubstituted or mono-, di- or trisubstituted independently of one another by R14;
—($C_6$-$C_{14}$)-aryl, wherein aryl is unsubstituted or mono-, di-, tri- or four times substituted independently of one another by R13; and
—($C_4$-$C_{14}$)-heteroaryl, wherein heteroaryl is unsubstituted or mono-, di-, tri- or four times substituted independently of one another by R13;

J is selected from a covalent bond;
—($C_1$-$C_6$)-alkylene, wherein alkylene is unsubstituted or mono-, di- or trisubstituted independently of one another by R14;
—($C_2$-$C_6$)-alkenylene, wherein alkenylene is unsubstituted or mono-, di- or trisubstituted independently of one another by R14,
—($C_2$-$C_6$)-alkynylene, wherein alkynylene is unsubstituted or mono-, di- or trisubstituted independently of one another by R14,
—($C_3$-$C_8$)-cycloalkyl, wherein cycloalkyl is unsubstituted or mono-, di- or trisubstituted independently of one another by R14;
—($C_6$-$C_{14}$)-aryl, wherein aryl is unsubstituted or mono-, di-, tri- or four times substituted independently of one another by R13; and
—($C_4$-$C_{14}$)-heteroaryl, wherein heteroaryl is unsubstituted or mono-, di-, tri- or four times substituted independently of one another by R13;

T is selected from a covalent bond;
—($C_1$-$C_6$)-alkylene, wherein alkylene is unsubstituted or mono-, di- or trisubstituted independently of one another by R14;
—($C_3$-$C_8$)-cycloalkyl, wherein cycloalkyl is unsubstituted or mono-, di- or trisubstituted independently of one another by R14;
—($C_6$-$C_{14}$)-aryl, wherein aryl is unsubstituted or mono-, di-, tri- or four times substituted independently of one another by R13; and
—($C_4$-$C_{14}$)-heteroaryl, wherein heteroaryl is unsubstituted or mono-, di-, tri- or four times substituted independently of one another by R13;

R0, R1, R2, R3, and R4 are identical or different, and are independently selected from:
a) hydrogen atom,
b) —($C_1$-$C_4$)-alkyl, wherein alkyl is unsubstituted or substituted one to three times by R13,
c) halogen,
d) phenyloxy-, wherein phenyloxy is unsubstituted or substituted one to three times by R13,
e) —($C_1$-$C_3$)-fluoroalkyl,
f) —N(R10)-($C_1$-$C_4$)-alkyl, wherein alkyl is unsubstituted or substituted one to three times by R13,
g) —($C_6$-$C_{14}$)-aryl, wherein aryl is unsubstituted or mono-, di-, tri- or four times substituted independently of one another by R13,
h) —($C_4$-$C_{14}$)-heteroaryl, wherein heteroaryl is unsubstituted or mono-, di-, tri- or four times substituted independently of one another by R13,
i) —($C_3$-$C_8$)-cycloalkyl, wherein said cycloalkyl is unsubstituted or mono-, di-, tri- or four times substituted independently of one another by R13,
j) a 3- to 7-membered cyclic residue, containing 1, 2, 3 or 4 heteroatoms selected from nitrogen, sulphur, and oxygen, wherein said cyclic residue is unsubstituted or mono-, di-, tri- or four times substituted independently of one another by R13,
k) —O—$CF_3$,
l) —O—($C_1$-$C_4$)-alkyl, wherein alkyl is unsubstituted or substituted one to three times by R13,
m) —$NO_2$,
n) —CN,
o) —OH,
p) —C(O)—R10,
q) —C(O)—O—R11,
r) —C(O)—N(R11)-R12,
s) —N(R11)-R12,
t) —N(R10)-$SO_2$—R10,
u) —S—R10,
v) —$SO_n$—R10, wherein n is 1 or 2,
w) —$SO_2$—N(R11)-R12, and
x) —O—$SO_2$—R13;
wherein at least one of R1, R2, R3 or R4 is absent when at least one of A1, A2, A3 or A4 is a nitrogen atom, or
R1 and R2, R2 and R3, or R3 and R4 form, together with the atoms with which they are attached, a 5- or 8-membered ring, containing up to 0, 1, 2, 3 or 4 heteroatoms selected from nitrogen, sulphur or oxygen, wherein said ring is unsubstituted or substituted one, two, three or four times by R14;
R5 and R6 are identical or different, and are independently selected from:
a) —($C_1$-$C_4$)-alkyl, wherein alkyl is unsubstituted or substituted one to three times by R13,
b) phenyloxy-, wherein phenyloxy is unsubstituted or substituted one to three times by R13,
c) —($C_1$-$C_3$)-fluoroalkyl,
d) —N(R10)-($C_1$-$C_4$)-alkyl, wherein alkyl is unsubstituted or substituted one to three times by R13,
e) —($C_6$-$C_{14}$)-aryl, wherein aryl is unsubstituted or mono-, di-, tri- or four times substituted independently of one another by R13,
f) —($C_4$-$C_{14}$)-heteroaryl, wherein heteroaryl is unsubstituted or mono-, di-, tri- or four times substituted independently of one another by R13,
g) —($C_3$-$C_8$)-cycloalkyl, wherein said cycloalkyl is unsubstituted or mono-, di-, tri- or four times substituted independently of one another by R13,
h) a 3- to 7-membered cyclic residue, containing 1, 2, 3 or 4 heteroatoms selected from nitrogen, sulphur, and oxygen, wherein said cyclic residue is unsubstituted or mono-, di-, tri- or four times substituted independently of one another by R13,
i) —C(O)—R10,
j) —C(O)—O—R11,
k) —C(O)—N(R11)-R12,
l) —$SO_n$—R10, wherein n is 1 or 2, and
m) —$SO_2$—N(R11)-R12;
R10 is selected from hydrogen atom, —($C_1$-$C_3$)-fluoroalkyl, and —($C_1$-$C_6$)-alkyl;
R11 and R12 are identical or different, and are independently selected from:
a) hydrogen atom,
b) —($C_1$-$C_6$)-alkyl, wherein alkyl is unsubstituted or mono-, di- or trisubstituted independently of one another by R13,
c) —($C_6$-$C_{14}$)-aryl-, wherein aryl is unsubstituted or mono-, di- or trisubstituted independently of one another by R13, and
d) —($C_4$-$C_{14}$)-heteroaryl, wherein heteroaryl is unsubstituted or mono-, di- or trisubstituted independently of one another by R13;
R13 is selected from halogen, —$NO_2$, —CN, =O, —OH, —($C_1$-$C_8$)-alkyl, —($C_1$-$C_8$)-alkoxy, —$CF_3$, phenyloxy-, —C(O)—R10, —C(O)—O—R17, —C(O)—N(R17)-R18, —N(R17)-R18, —N(R10)-$SO_2$—R10, —S—R10, —$SO_n$—R10, wherein n is 1 or 2, —$SO_2$—N(R17)-R18, —($C_6$-$C_{14}$)-aryl, wherein aryl is unsubstituted or mono-, di- or trisubstituted independently of one another by R14, —($C_4$-$C_{14}$)-heteroaryl, wherein heteroaryl is unsubstituted or mono-, di- or trisubstituted independently of one another by R14, —($C_3$-$C_8$)-cycloalkyl, wherein said cycloalkyl is unsubstituted or mono-, di- or trisubstituted independently of one another by R14, or a 3- to 7-membered cyclic residue, containing up to 1, 2, 3 or 4 heteroatoms chosen from nitrogen, sulphur or oxygen, wherein said cyclic residue is unsubstituted or mono-, di- or trisubstituted independently of one another by R14;
R14 is selected from halogen, —OH, =O, —CN, —$CF_3$, —($C_1$-$C_8$)-alkyl, —($C_1$-$C_4$)-alkoxy, —$NO_2$, —C(O)—OH, —N(R11)-R12, —C(O)—O—($C_1$-$C_4$)-alkyl, —($C_1$-$C_8$)-alkylsulfonyl, —C(O)—NH—($C_1$-$C_8$)-alkyl, —C(O)—N[($C_1$-$C_8$)-alkyl]$_2$, —C(O)—$NH_2$, —S—R10, —N(R10)-C(O)—NH—($C_1$-$C_8$)-alkyl, and —N(R10)-C(O)—N[($C_1$-$C_8$)-alkyl]$_2$;
R17 and R18 are identical or different, and are independently selected from:
a) hydrogen atom,
b) —($C_1$-$C_6$)-alkyl,
c) —($C_6$-$C_{14}$)-aryl-, and
d) —($C_4$-$C_{14}$)-heteroaryl,
said process comprises reacting a compound of formula II

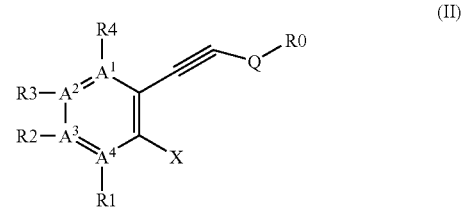

wherein R0, R1, R2, R3, R4, A1, A2, A3, R4 and Q are as defined in formula I, and X is selected from Cl, Br, I, triflate, nonaflate, tosylate, alkyl sulfonate and aryl sulfonate, with a compound of formula III or any salts thereof,

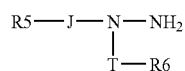
(III)

wherein J, T, R5 and R6 are as defined in formula I,
in the presence of a transition metal compound selected from: palladium (II) chloride, palladium (II) bromide, palladium (II) iodide, palladium (II) acetate, palladium (II) trifluoroacetate, tris(dibenzylideneacetone)di-palladium(0), tris(dibenzylideneacetone)di-palladium(0) chloroform adduct, bis(dibenzylideneacetone)palladium (0), bis(triphenyl-phosphine)palladium (II) chloride, and tetrakis(triphenylphosphine)palladium (0);
in the presence of a phosphine ligand selected from: tri-tert-butylphosphine, tri-tert-butylphosphine tetrafluoroborate salt, tricyclohexylphosphine, dicyclohexlphenylphosphine, methyldiphenylphosphine, dimethylphenyl-phosphine, trimethylphosphine, triethylphosphine, triphenylphosphine, 2-dicyclohexylphosphino-2',4',6'-triisopropyl-1,1'-biphenyl, and 2,2'-bis(di-tert-butylphosphino)biphenyl;
to give a compound of formula I and optionally, the compound of formula I is converted to its physiologically tolerated salt.

2. The process according to claim 1, wherein a compound of formula I is prepared, wherein A1, A2, A3 and A4 form together with the two carbon atoms in formula I a benzene, pyrazine, pyridazine, pyridine, pyrimidine, triazine or tetrazine ring,
Q is selected from a covalent bond;
—($C_1$-$C_6$)-alkylene, wherein alkylene is unsubstituted or mono-, di- or trisubstituted independently of one another by R14;
—($C_3$-$C_6$)-cycloalkyl, wherein cycloalkyl is unsubstituted or mono-, di- or trisubstituted independently of one another by R14;
phenyl, wherein phenyl is unsubstituted or mono-, di-, tri- or four times substituted independently of one another by R13; and
—($C_4$-$C_{14}$)-heteroaryl, wherein heteroaryl is selected from acridinyl, azaindole (1H-pyrrolopyridinyl), azabenzimidazolyl, azaspirodecanyl, azepinyl, azetidinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, carbazolyl, 4aH-carbazolyl, carbolinyl, chromanyl, chromenyl, cinnolinyl, decahydrochinolinyl, 4,5-dihydrooxazolinyl, dioxazolyl, dioxazinyl, 1,3-dioxolanyl, 1,3-dioxolenyl, 3,3-dioxo[1,3,4]oxathiazinyl, 6H-1,5,2-dithiazinyl, dihydrofuro[2,3-b]-tetrahydrofuranyl, furanyl, furazanyl, imidazolidinyl, imidazolinyl, imidazolyl, indanyl, 1H-indazolyl, indolinyl, indolizinyl, indolyl, 3H-indolyl, isobenzofuranyl, isochromanyl, isoindazolyl, isoindolinyl, isoindolyl, isoquinolinyl, isothiazolyl, isothiazolidinyl, isothiazolinyl, isoxazolyl, isoxazolinyl, isoxazolidinyl, 2-isoxazolinyl, ketopiperazinyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, 1,2-oxathiepanyl, 1,2-oxathiolanyl, 1,4-oxazepanyl, 1,4-oxazepinyl, 1,2-oxazinyl, 1,3-oxazinyl, 1,4-oxazinyl, oxazolidinyl, oxazolinyl, oxazolyl, oxetanyl, oxocanyl, phenanthridinyl, phenanthrolinyl, phenazinyl, phenothiazinyl, phenoxathiinyl, phenoxazinyl, phthalazinyl, piperazinyl, piperidinyl, pteridinyl, purinyl, pyranyl, pyrazinyl, pyrazolidinyl, pyrazolinyl, pyrazolyl, pyrazolo[3,4-b]pyridine, pyridazinyl, pyridooxazolyl, pyridoimidazolyl, pyridothiazolyl, pyridinyl, pyridyl, pyrimidinyl, pyrrolidinyl, pyrrolidinonyl, pyrrolinyl, 2H-pyrrolyl, pyrrolyl, quinazolinyl, quinolinyl, 4H-quinolizinyl, quinoxalinyl, quinuclidinyl, tetrahydro-furanyl, tetrahydroisoquinolinyl, tetrahydroquinolinyl, tetrahydrofuranyl, tetra-hydropyranyl, tetrahydropyridinyl, tetrahydrothiophenyl, tetrazinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, 1,2-thiazinyl, 1,3-thiazinyl, 1,4-thiazinyl, 1,3-thiazolyl, thiazolyl, thiazolidinyl, thiazolinyl, thienyl, thietanyl, thienothiazolyl, thieno-oxazolyl, thienoimidazolyl, thietanyl, thiomorpholinyl, thiophenolyl, thiophenyl, thiopyranyl, 1,2,3-triazinyl, 1,2,4-triazinyl, 1,3,5-triazinyl, 1,2,3-triazolyl, 1,2,3-triazolyl, 1,2,4-triazolyl, 1,2,5-triazolyl, 1,3,4-triazolyl and xanthenyl, and wherein heteroaryl is unsubstituted or mono-, di-, tri- or four times substituted independently of one another by R13;
J is selected from a covalent bond;
—($C_1$-$C_6$)-alkylene, wherein alkylene is unsubstituted or mono-, di- or trisubstituted independently of one another by R14;
—($C_2$-$C_6$)-alkenylene, wherein alkenylene is unsubstituted or mono-, di- or trisubstituted independently of one another by R14,
—($C_3$-$C_6$)-cycloalkyl, wherein cycloalkyl is unsubstituted or mono-, di- or trisubstituted independently of one another by R14;
phenyl, wherein phenyl is unsubstituted or mono-, di-, tri- or four times substituted independently of one another by R13; and
—($C_4$-$C_{14}$)-heteroaryl, wherein heteroaryl is as defined above and is unsubstituted or mono-, di-, tri- or four times substituted independently of one another by R13;
T is selected from a covalent bond;
—($C_1$-$C_6$)-alkylene, wherein alkylene is unsubstituted or mono-, di- or trisubstituted independently of one another by R14;
—($C_3$-$C_6$)-cycloalkyl, wherein cycloalkyl is unsubstituted or mono-, di- or trisubstituted independently of one another by R14;
phenyl, wherein phenyl is unsubstituted or mono-, di-, tri- or four times substituted independently of one another by R13; and
—($C_4$-$C_{14}$)-heteroaryl, wherein heteroaryl is as defined above and is unsubstituted or mono-, di-, tri- or four times substituted independently of one another by R13;
R0, R1, R2, R3, and R4 are identical or different and are independently selected from:
a) hydrogen atom,
b) F,
c) Cl or Br,
d) —($C_1$-$C_4$)-alkyl, wherein alkyl is unsubstituted or substituted one, two or three times by R13,
e) —($C_1$-$C_3$)-fluoroalkyl,
f) phenyl or naphthyl, wherein phenyl or naphthyl are unsubstituted or substituted one, two or three times by R13,
g) —($C_4$-$C_{14}$)-heteroaryl, wherein heteroaryl is as defined above and is unsubstituted or mono-, di-, tri- or four times substituted independently of one another by R13,
h) —($C_3$-$C_6$)-cycloalkyl, wherein said cycloalkyl is unsubstituted or mono-, di-, tri- or four times substituted independently of one another by R13,
i) a 3- to 7-membered cyclic residue selected from azepine, azetidine, aziridine, azirine, 1,4 diazepane, 1,2-diazepine, 1,3-diazepine, 1,4-diazepine, diaziridine, diazirine, dioxazole, dioxazine, dioxole, 1,3-dioxolene, 1,3-dioxolane, furan, imidazole, imidazoline, imidazolidine, isothiazole, isothiazolidine, isothiazoline, isoxazole, isoxazoline, isoxazolidine, 2-isoxazoline, keto-morpholine, ketopiperazine, morpholine, 1,2-oxa-thiepane, 1,2-oxathiolane, 1,4-oxazepane, 1,2-oxazine, 1,3-oxazine, 1,4-oxazine, oxazole, oxaziridine, oxetan, oxirane, piperazine, piperidine, pyran, pyrazine, pyrazole, pyrazoline, pyrazolidine, pyridazine, pyridine, pyrimidine, pyrrole, pyrrolidine, pyrrolidinone, pyrroline, tetrahydrofuran, tetrahydropyran, tetrahydropyridine, tetrazine, tetrazole, thiadiazine thiadiazole, 1,2-thiazine, 1,3-thiazine, 1,4-thiazine, 1,3-thiazole, thiazole, thiazolidine, thiazoline, thienyl, thietan, thiomorpholine, thiopyran, 1,2,3-triazine, 1,2,4-triazine, 1,3,5-triazine, 1,2,3-triazole or 1,2,4-triazole, and is unsubstituted or mono-, di-, tri- or four times substituted independently of one another by R13, j) —O—CF$_3$,
k) —O—(C$_1$-C$_4$)-alkyl, wherein alkyl is unsubstituted or substituted one, two or three times by R13,
l) —N(R10)-(C$_1$-C$_4$)-alkyl, wherein alkyl is unsubstituted or substituted one, two or three times by R13,
m) —CN,
n) —OH,
o) phenyloxy-, wherein phenyloxy is unsubstituted or substituted one, two or three times by R13,
p) —C(O)—O—R11,
q) —C(O)—N(R11)-R12,
r) —N(R11)-R12,
s) —N(R10)-SO$_2$—R10,
t) —S—R10,
u) —SO$_n$—R10, wherein n is 1 or 2,
v) —SO$_2$—N(R11)-R12,
w) —C(O)—R10, and
x) —O—SO$_2$—R13;

wherein at least one of R1, R2, R3 or R4 is absent when at least one of A1, A2, A3 or A4 is a nitrogen atom;

R5 and R6 are identical or different, and are independently selected from:
a) —(C$_1$-C$_4$)-alkyl, wherein alkyl is unsubstituted or substituted one, two or three times by R13,
b) —(C$_1$-C$_3$)-fluoroalkyl,
c) phenyl or naphthyl, wherein phenyl or naphthyl are unsubstituted or substituted one, two or three times by R13,
d) —(C$_4$-C$_{14}$)-heteroaryl, wherein heteroaryl is as defined above and is unsubstituted or mono-, di-, tri- or four times independently of one another by R13,
e) —(C$_3$-C$_6$)-cycloalkyl, wherein said cycloalkyl is unsubstituted or mono-, di-, tri- or four times substituted independently of one another by R13,
f) a 3- to 7-membered cyclic residue selected from azepine, azetidine, aziridine, azirine, 1,4 diazepane, 1,2-diazepine, 1,3-diazepine, 1,4-diazepine, diaziridine, diazirine, dioxazole, dioxazine, dioxole, 1,3-dioxolene, 1,3-dioxolane, furan, imidazole, imidazoline, imidazolidine, isothiazole, isothiazolidine, isothiazoline, isoxazole, isoxazoline, isoxazolidine, 2-isoxazoline, keto-morpholine, ketopiperazine, morpholine, 1,2-oxa-thiepane, 1,2-oxathiolane, 1,4-oxazepane, 1,2-oxazine, 1,3-oxazine, 1,4-oxazine, oxazole, oxaziridine, oxetan, oxirane, piperazine, piperidine, pyran, pyrazine, pyrazole, pyrazoline, pyrazolidine, pyridazine, pyridine, pyrimidine, pyrrole, pyrrolidine, pyrrolidinone, pyrroline, tetrahydrofuran, tetrahydropyran, tetrahydropyridine, tetrazine, tetrazole, thiadiazine thiadiazole, 1,2-thiazine, 1,3-thiazine, 1,4-thiazine, 1,3-thiazole, thiazole, thiazolidine, thiazoline, thienyl, thietan, thiomorpholine, thiopyran, 1,2,3-triazine, 1,2,4-triazine, 1,3,5-triazine, 1,2,3-triazole or 1,2,4-triazole, and is unsubstituted or mono-, di-, tri- or four times substituted independently of one another by R13, g) —N(R10)-(C$_1$-C$_4$)-alkyl, wherein alkyl is unsubstituted or substituted one, two or three times by R13,
h) phenyloxy, wherein phenyloxy is unsubstituted or substituted one, two or three times by R13
i) —C(O)—O—R11,
j) —C(O)—N(R11)-R12,
k) —SO$_n$—R10, wherein n is 1 or 2,
l) —SO$_2$—N(R11)-R12, and
m) —C(O)—R10;

R10 is hydrogen atom, —(C$_1$-C$_3$)-fluoroalkyl, or —(C$_1$-C$_6$)-alkyl,

R11 and R12 are identical or different and are independently selected from:
a) hydrogen atom,
b) —(C$_1$-C$_4$)-alkyl, wherein alkyl is unsubstituted or mono-, di- or trisubstituted independently of one another by R13,
c) phenyl, wherein phenyl is unsubstituted or mono-, di- or trisubstituted independently of one another by R13, and
d) —(C$_4$-C$_{14}$)-heteroaryl, wherein heteroaryl is as defined above and is unsubstituted or mono-, di- or trisubstituted independently of one another by R13;

R13 is selected from F, Cl, —CN, =O, —OH, —(C$_1$-C$_8$)-alkyl, —(C$_1$-C$_8$)-alkoxy, —CF$_3$, phenyloxy-, —C(O)—R10, —C(O)—O—R17, —C(O)—N(R17)-R18, —N(R17)-R18, —N(R10)-SO$_2$—R10, —S—R10, —SO$_n$—R10, wherein n is 1 or 2, —SO$_2$—N(R17)-R18, phenyl, wherein phenyl is unsubstituted or mono-, di- or trisubstituted independently of one another by R14, —(C$_4$-C$_{14}$)-heteroaryl, wherein heteroaryl is as defined above and is unsubstituted or mono-, di- or trisubstituted independently of one another by R14, —(C$_3$-C$_6$)-cycloalkyl, wherein said cycloalkyl is unsubstituted or mono-, di- or trisubstituted independently of one another by R14, and a 3- to 7-membered cyclic residue, which is as defined above and is unsubstituted or mono-, di- or trisubstituted independently of one another by R14;

R14 is selected from F, Cl, —OH, =O, —CN, —CF$_3$, —(C$_1$-C$_8$)-alkyl, —(C$_1$-C$_4$)-alkoxy, —C(O)—OH, —N(R11)-R12, —C(O)—O—(C$_1$-C$_4$)-alkyl, —(C$_1$-C$_8$)-alkylsulfonyl, —C(O)—NH$_2$, —C(O)—NH—(C$_1$-C$_8$)-alkyl, —C(O)—N[(C$_1$-C$_8$)-alkyl]$_2$, —S—R10, —N(R10)-C(O)—NH—(C$_1$-C$_8$)-alkyl and —N(R10)-C(O)—N[(C$_1$-C$_8$)-alkyl]$_2$;

R17 and R18 are identical or different, and are independently selected from:
a) hydrogen atom,
b) —(C$_1$-C$_4$)-alkyl,
c) phenyl, and
d) —(C$_4$-C$_{14}$)-heteroaryl, wherein heteroaryl is as defined above; and X is Cl, Br, I, triflate, nonaflate or tosylate.

3. The process according to claim 1, wherein A1, A2, A3 and A4 form together with the two carbon atoms in formula I a benzene or pyridine ring, Q is a covalent bond, methylene, ethylene, phenyl or pyridyl;
J is a covalent bond, methylene, ethylene, phenyl or pyridyl,
T is a covalent bond, methylene, ethylene, phenyl or pyridyl,
R0, R1, R2, R3, and R4 are identical or different and are independently selected from:
a) hydrogen atom,
b) F, c) Cl or Br,
d) —($C_1$-$C_4$)-alkyl,
e) —($C_1$-$C_3$)-fluoroalkyl,
f) phenyl,
g) pyridyl,
h) —($C_3$-$C_6$)-cycloalkyl,
k) —O—($C_1$-$C_4$)-alkyl, and
l) —C(O)—O—R11;
provided that at least one of R1, R2, R3 or R4 is absent when at least one of A1, A2, A3 or A4 is a nitrogen atom;
R5 and R6 are identical or different, and are independently selected from:
a) —($C_1$-$C_4$)-alkyl,
b) —($C_1$-$C_3$)-fluoroalkyl,
c) phenyl,
d) pyridyl,
e) —($C_3$-$C_6$)-cycloalkyl,
f) —C(O)—O—R11;
R11 is hydrogen atom or —($C_1$-$C_4$)-alkyl; and
X is Cl, Br, I or tosylate.

4. The process according to claim 1, wherein the compound according to formula I is selected from: Phenyl-(2-phenyl-indol-1-yl)-carbamic acid tert-butyl ester; (6-Fluoro-2-phenyl-indol-1-yl)-phenyl-carbamic acid tert-butyl ester; Phenyl-(2-phenyl-5-trifluoromethyl-indol-1-yl)-carbamic acid tert-butyl ester; (6-Methoxy-2-phenyl-indol-1-yl)-phenyl-carbamic acid tert-butyl ester; Methyl-(2-phenyl-indol-1-yl)-carbamic acid tert-butyl ester; Phenyl-(2-phenyl-indol-1-yl)-carbamic acid ethyl ester; Phenyl-(2-pyridin-2-yl-indol-1-yl)-carbamic acid tert-butyl ester; 1-(tert-Butoxycarbonyl-phenyl-amino)-1H-indole-2-carboxylic acid tert-butyl ester; Phenyl-(2-phenyl-pyrrolo[3,2-c]pyridin-1-yl)-carbamic acid tert-butyl ester; and 1-(tert-Butoxycarbonyl-phenyl-amino)-2-cyclopropyl-1H-indole-6-carboxylic acid tert-butyl ester.

5. The process according to claim 1, further comprising conducting the process in the presence of a base wherein said base is selected from the group consisting of carbonates, phosphates, fluorides, alkoxides, and hydroxides, with a suitable metal or alkali metal as counterion.

6. The process according to claim 5, wherein the base is selected from the group consisting of potassium carbonate, potassium phosphate, and cesium carbonate.

7. The process according to claim 1, further comprising conducting the process in the presence of a solvent wherein said solvent is selected from the group consisting of N,N-dimethyl-formamide, N-methylpyrrolidinone, dimethylacetamide, dimethylsulfoxide, 1,2-dimethoxyethane, triethylamine, and pyridine.

8. The process according to claim 1, wherein the reaction between the compounds of formula II and formula III is conducted in the temperature range of 60° C. to 150° C.

9. The process according to claim 8, wherein the reaction between the compounds of formula II and formula III is conducted in the temperature range of 100° C. to 130° C.

10. The process according to claim 1, wherein said phosphine ligand is selected from the group consisting of tri-tert-butylphosphine, tri-tert-butylphosphine tetrafluoroborate salt, tricyclohexylphosphine, and 2-dicyclohexylphosphino-2',4',6'-triisopropyl-1,1'-biphenyl.

11. The process according to claim 1, wherein said phosphine ligand is tri-tert-butylphosphine or tri-tert-butylphosphine tetrafluoroborate salt.

* * * * *